(12) United States Patent
Ogembo et al.

(10) Patent No.: US 12,303,559 B2
(45) Date of Patent: *May 20, 2025

(54) MULTIVALENT EPSTEIN-BARR VIRUS-LIKE PARTICLES AND USES THEREOF

(71) Applicant: CITY OF HOPE, Duarte, CA (US)

(72) Inventors: Javier Gordon Ogembo, San Dimas, CA (US); Lorraine Zvichapera Mutsvunguma, Duarte, CA (US); Felix Wussow, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/612,771

(22) Filed: Mar. 21, 2024

(65) Prior Publication Data

US 2024/0358813 A1  Oct. 31, 2024

Related U.S. Application Data

(63) Continuation of application No. 16/647,705, filed as application No. PCT/US2018/051268 on Sep. 16, 2018, now Pat. No. 11,964,006.

(60) Provisional application No. 62/559,528, filed on Sep. 16, 2017.

(51) Int. Cl.
| | | |
|---|---|---|
| *A61K 39/12* | (2006.01) | |
| *C07K 16/00* | (2006.01) | |
| *C07K 16/08* | (2006.01) | |
| *C12N 7/00* | (2006.01) | |
| *A61K 39/00* | (2006.01) | |

(52) U.S. Cl.
CPC ............ *A61K 39/12* (2013.01); *C07K 16/085* (2013.01); *C12N 7/00* (2013.01); *A61K 2039/55505* (2013.01); *A61K 2039/55572* (2013.01); *C07K 2317/76* (2013.01); *C12N 2710/16222* (2013.01); *C12N 2710/16223* (2013.01); *C12N 2710/16234* (2013.01)

(58) Field of Classification Search
None
See application file for complete search history.

(56) References Cited

U.S. PATENT DOCUMENTS

| | | | |
|---|---|---|---|
| 6,004,777 A | 12/1999 | Tartaglia et al. | |
| 10,314,906 B2 | 6/2019 | Ogembo et al. | |
| 10,960,072 B2 | 3/2021 | Ogembo et al. | |
| 11,964,006 B2 * | 4/2024 | Ogembo | A61P 31/20 |

FOREIGN PATENT DOCUMENTS

| | | |
|---|---|---|
| EP | 2468768 A2 | 6/2012 |
| WO | 2016/149384 A1 | 9/2016 |

OTHER PUBLICATIONS

Ogembo et al., Journal of Translational Medicine, 2015.*
Babcock, G. J., et al., "EBV Persistence in Memory B Cells In Vivo," Immunity 9:395-404 (1998).
Cohen, J. I., et al., "Epstein-Barr Virus: An Important Vaccine Target for Cancer Prevention," Sci. Transl. Med. 3(107):107fs7 (2011).
Cohen, J. I., "Epstein-Barr Virus Vaccines," Clin. Transl. Immunol. 4:e32 (2015).
Connolly, S. A., et al., "Fusing Structure and Function: A Structural View of the Herpesvirus Entry Machinery," Nat. Rev. Microbiol. 9(5):369-381 (2011).
Cui, X., et al., "Rabbits Immunized with Epstein-Barr Virus gH/gL of GB Recombinant Proteins Elicit Higher Serum Virus Neutralizing Activity than gp350," Vaccine 34:4050-4055 (2016).
Fujiwara, S., et al., "Modeling EBV Infection and Pathogenesis in New-Generation Humanized Mice," Exp. Mol. Med. 47:e135 (2015).
Germain, R. N., "The Ins and Outs of Antigen Processing and Presentation," Nature 322:687-689 (1986).
Goedert, J. J., et al., "Spectrum of AIDS-Associated Malignant Disorders," Lancet 351:1833-1839 (1998).
Jangalwe, S., et al., "Improved B Cell Development in Humanized NOD-scid IL2Ry$^{null}$ Mice Transgenically Expressing Human Stem Cell Factor, Granulocyte-Macrophage Colony-Stimulating Factor and Interleukin-3," Immun. Inflamm. Dis. 4(4):427-440 (2016).
Janz, A., et al., "Infectious Epstein-Barr Virus Lacking Major Glycoprotein BLLF1 (gp350/220) Demonstrates the Existence of Additional Viral Ligands," J. Virol. 74(21):10142-10152 (2000).
Johannsen, E., et al., "Proteins of Purified Epstein-Barr Virus," PNAS 101(46):16286-16291 (2004).
Kim, J. H., et al., "High Cleavage Efficiency of a 2A Peptide Derived from Porcine Teschovirus-1 in Human Cell Lines, Zebrafish and Mice," PLoS One 6(4):e18556 (2011).
Miller, N., et al., "A Monoclonal Antibody to Glycoprotein gp85 Inhibits Fusion but Not Attachment of Epstein-Barr Virus," J. Virol. 62(7):2366-2372 (1988).
Molesworth, S. J., et al., "Epstein-Barr Virus gH is Essential for Penetration of B Cells but Also Plays a Role in Attachment of Virus to Epithelial Cells," J. Virol. 74(14):6324-6332 (2000).
Moutschen, M., et al., "Phase I/II Studies to Evaluate Safety and Immunogenicity of a Recombinant gp350 Epstein-Barr Virus Vaccine in Healthy Adults," Vaccine 25:4697-4705 (2007).

(Continued)

*Primary Examiner* — Agnieszka Boesen
(74) *Attorney, Agent, or Firm* — Perkins Coie LLP; Lara J. Dueppen; Gregory J. Logan

(57) ABSTRACT

Disclosed are vaccine compositions comprising a VLP comprising two or more EBV envelope glycoproteins and one or more T cell antigens and methods of preventing or treating EBV infections using the vaccine compositions. Also disclosed is an expression system or a single expression vector for co-expressing two or more EBV envelope glycoproteins simultaneously to generate a VLP vaccine. The expression system may include a single vector inserted with two or more nucleic acid sequences that encode two or more EBV envelope glycoproteins linked by one or more linking sequences such that the EBV envelope glycoproteins are co-expressed simultaneously.

20 Claims, 24 Drawing Sheets

Specification includes a Sequence Listing.

(56) References Cited

OTHER PUBLICATIONS

Ogembo, J. G., et al., "Human Complement Receptor Type 1/CD35 is an Epstein-Barr Virus Receptor," Cell Rep. 3(2):371-385 (2013).
Ogembo, J. G., et al., "A Chimeric EBV gp350/220-Based VLP Replicates the Virion B-Cell Attachment Mechanism and Elicits Long-Lasting Neutralizing Antibodies in Mice," J. Transl. Med. 13:50 (2015).
Pavlova, S., et al., "An Epstein-Barr Virus Mutant Produces Immunogenic Defective Particles Devoid of Viral DNA," J. Virol. 87(4):2011-2022 (2012).
Perez, E. M., et al., "Novel Epstein-Barr Virus-Like Particles Incorporating gH/gL-EBNA1 or GB-LMP2 Induce High Neutralizing Antibody Titers and EBV-Specific T-Cell Responses in Immunized Mice," Oncotarget 8(12):19255-19273 (2017).
Ray, G., et al., "C-Terminal DxD-Containing Sequences within Paramyxovirus Nucleocapsid Proteins Determine Matrix Protein Compatibility and Can Direct Foreign Proteins into Budding Particles," J. Virol. 90(7):3650-3660 (2016).
Rees, L., et al., "A Phase I Trial of Epstein-Barr Virus Gp350 Vaccine for Children with Chronic Kidney Disease Awaiting Transplantation," Transplant. 88:1025-1029 (2009).
Ruiss, R., et al., "A Virus-Like Particle-Based Epstein-Barr Virus Vaccine," J. Virol. 85(24):13105-13113 (2011).
Sokal, E. M., et al., "Recombinant gp350 Vaccine for Infectious Mononucleosis: A Phase 2, Randomized, Double-Blind, Placebo-Controlled Trial to Evaluate the Safety, Immunogenicity, and Efficacy of an Epstein-Barr Virus Vaccine in Healthy Young Adults," J. Infect. Dis. 196:1749-1753 (2007).
United States Patent and Trademark Office, International Search Report and Written Opinion dated Feb. 5, 2019 for International Patent Application No. PCT/US2018/051268, 10 pages.
Wang, X., et al., "Epstein-Barr Virus Lacking Glycoprotein gp42 Can Bind to B Cells but is Not Able to Infect," J. Virol. 72(1):158-163 (1998).Z.

\* cited by examiner

FIG. 2C

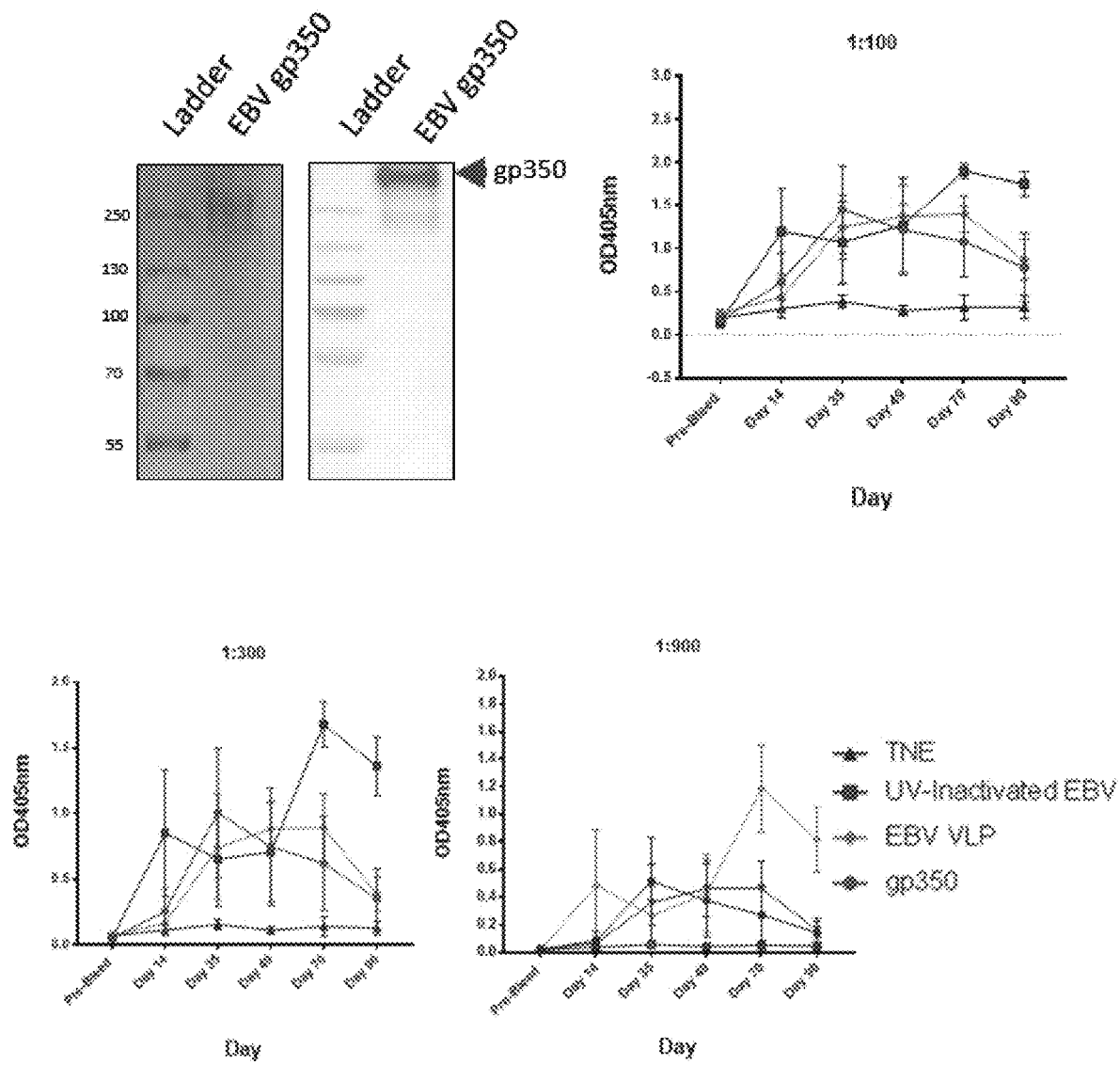

B. gB

C. gp42

C. CFSE Proliferation
Sample #19

MULTIVALENT EPSTEIN-BARR VIRUS-LIKE PARTICLES AND USES THEREOF

PRIORITY CLAIM

This application is a continuation of U.S. application Ser. No. 16/647,705, filed Mar. 16, 2020, which is a U.S. National Phase Application of International Application No. PCT/US18/51268, filed Sep. 16, 20218, which claims priority to U.S. Provisional Application No. 62/559,528, filed Sep. 16, 2017, all of which are incorporated by reference herein in their entirety, including drawings.

STATEMENT OF GOVERNMENT INTEREST

This invention was made with government support under R21 CA205106 awarded by the National Institutes of Health. The government has certain rights in the invention.

SEQUENCE LISTING

This application contains a ST.26 compliant Sequence Listing, which was submitted in XML format via Patent Center, and is hereby incorporated by reference in its entirety. The XML copy, created on Jun. 18, 2024, is named SubstituteSequenceListing.xml and is 6,000 bytes in size.

BACKGROUND

Epstein-Barr virus (EBV) infection of over 90% of the human population is associated with the development of several lymphoproliferative disorders and over 200,000 cancer cases worldwide each year[1,2]. The etiology of EBV across the world is varied. In low-income settings, primary EBV infection typically occurs asymptomatically during early childhood[1]. However, in malaria-endemic regions such as equatorial Africa, childhood acquisition poses an increased risk of EBV+ Burkitt lymphoma (BL)[1]. In high-income settings such as the United States of America, primary EBV infection is delayed, but it causes acute infectious mononucleosis (IM) in 50-70% of adolescents with EBV primary infection, and significantly increases the risk of developing EBV+ Hodgkin lymphoma[1]. EBV is also highly associated with nasopharyngeal (China) and gastric carcinomas (Eastern Asia, Eastern Europe, and South America), reflecting the epithelial tropism of the virus[1]. Among infected individuals, EBV remains quiescent in memory B cells[13], but can reactivate and cause diseases under immunosuppression, as with malaria-associated BL, post-transplant lymphoproliferative disorders (PTLDs) in EBV-naïve children and adolescents receiving EBV+ organs, and AIDS-associated B-cell lymphomas[14].

Thus, EBV infection and its associated malignancies contribute to a significant public health burden for children and adults worldwide. There is no licensed prophylactic or therapeutic vaccine against EBV infection or its associated diseases. A panel of experts at a 2011 NIH EBV meeting concurred on the urgent need to develop an effective and safe vaccine to both prevent and treat EBV-associated malignancies and consequently impact public health worldwide[2].

Antibodies provide the first line of defense against viral infection. Neutralizing antibodies directed against EBV envelope glycoproteins involved in virus entry are present in humans, can prevent neonatal infection, and are generated in response to immunization of humans[3]. However, persistent EBV infection and the limited evidence of immune selection of viral antigenic variants indicate that in vivo neutralization of EBV infection is suboptimal. Previous candidate vaccines based on viral proteins have targeted only one arm of the immune system, either humoral using two or more glycoproteins (prophylactic vaccine) or T cell-mediated (therapeutic vaccine), and have shown low efficacy profiles[4]. Thus, it is important to develop a multivalent EBV vaccine that elicits robust antibody and T cell responses. The compositions and technology disclosed herein satisfy the need in the art.

SUMMARY

In one aspect, this disclosure relates to virus-like particles (VLPs) comprising two or more EBV envelope glycoproteins and one or more T cell antigens. In some embodiments, the EBV envelope glycoproteins include gp350, gB, gp42, gH, gL, gM, gN, BMRF2, BDLF2, BDLF3, BILF1, BILF2, and BARF1. In some embodiments, the T cell antigens include EBNA1, EBNA2, EBNA3a, EBNA3b, EBNA3c, EBNA-leader protein, and LMP2. In some embodiments, the VLP further comprises Newcastle Disease virus (NDV) structural proteins including fusion (F), matrix (M), nucleocapsid (NP), or a combination thereof.

In a related aspect, this disclosure relates to a vaccine composition or a pharmaceutical composition comprising a therapeutically effective amount of a single VLP comprising two or more EBV envelope glycoproteins and one or more T cell antigens. In some embodiments, the EBV envelope glycoproteins include gp350, gB, gp42, gH, gL, and any other known EBV envelope glycoproteins such as gM, gN, BMRF2, BDLF2, BDLF3, BILF2, BILF1, and BARF1. In some embodiments, the T cell antigens include EBV nuclear antigen 1 (EBNA1), EBNA2, EBNA3a, EBNA3b, EBNA3c, EBNA-leader protein, and/or late membrane protein (LMP2). In some embodiments, the VLP further comprises NDV structural proteins including fusion (F), matrix (M), nucleocapsid (NP), or a combination thereof. In some embodiments, the vaccine composition or the pharmaceutical composition further comprises one or more additional pharmaceutically acceptable antigens. In some embodiments, the vaccine composition or the pharmaceutical composition further comprises one or more adjuvants. In some embodiments, the vaccine composition or the pharmaceutical composition further comprises one or more pharmaceutically acceptable carriers.

In a related aspect, this disclosure relates to a method of preventing or treating an EBV infection or a condition associated with an EBV infection comprising administering to a subject in need thereof a therapeutically effective amount of the VLP, the vaccine composition or the pharmaceutical composition described above.

In a related aspect, this disclosure relates to an immunization regimen comprising administering to a subject in need thereof one or more doses of a therapeutically effective amount of the VLP, the vaccine composition or the pharmaceutical composition described above.

In a related aspect, this disclosure relates to utilization of these VLP as a platform to generate dendritic cells or T cell responses in cell culture (in vitro) that can be infused as a therapeutic treatment to a subject in need thereof one or more doses of a therapeutically effective amount of the cell therapy.

In another aspect, this disclosure relates to an expression system for co-expressing two or more EBV envelope glycoproteins. The expression system may include a single vector inserted with two or more nucleic acid sequences that encode two or more EBV envelope glycoproteins, linked by one or more linking sequences, such that the two or more EBV envelope glycoproteins can be co-expressed simultaneously, self-cleaved and/or self-processed to assemble into certain glycoprotein complex, e.g., gH/gL complex, gp42-gH/gL complex, gB-gH/gL complex, BMRF2/BDLF2 complex or synthesized mRNA. The vector can be a plasmid vector or a viral vector. In some embodiments, the linking sequences include IRES and nucleic acid sequences encoding 2A peptides that mediate ribosomal skipping and self-cleavage. In some embodiments, the vector is inserted with a single promoter before the two or more nucleic acid sequences such that the single promoter controls the expression of the two or more nucleic acid sequences.

BRIEF DESCRIPTION OF THE DRAWINGS

FIG. 1A shows transient transfection and selection of CHO cells transfected with gp350-F-gB-F-gp42-WT-gL-WT-gH-F. FIG. 1B shows flow cytometry analysis of sorted stable cells. FIG. 1C shows second flow cytometry analysis of CHO stable cells expressing five EBV glycoproteins.

FIGS. 2A-2C illustrate the production and characterization of Epstein-Barr virus-like particles (EB VLPs). FIG. 2A illustrates the process of generating stable cells producing VLPs. FIG. 2B shows representative stable cells producing VLPs stained with primary antibodies (1:200) 72A1 or E1D1 for 30 min, compared to unstained cells and cells stained with the isotype control alone. FIG. 2C illustrates another example of production and sucrose gradient purification of polyvalent EB VLPs.

FIG. 3A shows maturation of monocyte-derived dendritic cells (DCs) at various concentration of VLPs, from 1 μg/ml to 10 μg/ml. From top to bottom, the samples are unstained, 1 μg/ml VLP, 5 μg/ml VLP, and 10 μg/ml VLP. FIG. 3B shows EB VLP pulsed DCs stimulation of IFN-γ production and CD8 T cells proliferation.

FIG. 5A shows immunization and bleeding schedules for 6-8-week-old female BALB/c mice. A total of 9 groups of BALB/c were immunized with 10 μg of purified gp350, gB-LMP2, or gH/gL-EBNA1 VLPs or combination of gp350 and gB-LMP2; gp350 and gH/gL-EBNA1; gB-LMP2 and gH/gL-EBNA1; or gp350, gH/gL-EBNA1, and gB-LMP2 VLPs. Two groups were immunized with purified UV-inactivated EBV (10 μg) or TNE buffer as positive and negative controls, respectively. FIG. 5B shows that antibody titer in sera from immunized BALB/c mice determined using lysate from EBV-infected AGS cells as target, and detected by ELISA. For each group of the samples on D14 and D97, respectively, from left to right, the samples are gp350, gB-LMP2, gH/gL-EBNA1, gp350+gB-LMP2, gp350+gH/gL-EBNA1, gB-LMP2+gH/gL-EBNA1, gp350+gB-LMP2+gH/gL-EBNA1, and UV-inactivated EBV. FIG. 5C shows that pooled terminal bleed sera from 5 animals/immunization treatment were pre-incubated with eGFP-EBV, then incubated at 37° C. for 48 h with Raji cells; EBV-EGFP+ cells were enumerated by flow cytometry. Neutralizing anti-gp350 (72A1, dotted line) served as pos. control. TNE (negative control) was used to normalize percent infection. Mice immunized with a combination of all three EB VLPs (gp350, gB-LMP2, and gH/gL-EBNA1) was the most effective in neutralizing infection (23.8%), followed by gp350 (18.7%), gB (17.9%), or UV-inactivated EBV (16.6%). From left to right, the samples are gp350, gB-LMP2, gH/gL-EBNA1, gp350+gB-LMP2, gp350+gH/gL-EBNA1, gB-LMP2+gH/gL-EBNA1, gp350+gB-LMP2+gH/gL-EBNA1, and UV inactivated EBV. Thus, only sera from mice immunized with a mixture of all three VLPs neutralized over 50% of EBV infection (relative to neg. control) in vitro; this was more effective than gp350 ($p<0.012$) or all other immunogens ($p<0.0001$). Similar trends were observed in HEK293 cells (data not shown). These results suggest that an effective EBV prophylactic vaccine requires multiple glycoproteins. (Partly adapted from Perez et al. 2017[17])

FIG. 6A shows identification of components of EBV gp350-gB-gp42-gL-gH VLPs and NDV M and full-length NP (without EBNA1-LMP2). FIG. 6B shows identification of components of EB VLPs gp350-gB-gp42-gL-gH and NDV M and 26 aa of NP fused to truncated EBNA1 and full-length LMP2.

FIGS. 9A-9D show the evaluation of EBV-specific IgG antibodies response generated in EB VLPs immunized wild type New Zealand white rabbits. FIG. 9A shows the coomassie stain and immunoblot analysis of recombinant EBV gp350 and gp350-specific IgG titers from diluted sera (1:100, 1:300 and 1:900). FIG. 9B shows the coomassie stain and immunoblot analysis of recombinant EBV gB and gB-specific IgG titers from diluted sera (1:100, 1:300 and 1:900). FIG. 9C shows the coomassie stain and immunoblot analysis of recombinant EBV gp42 and gp42-specific IgG titers from diluted sera (1:100, 1:300 and 1:900). FIG. 9D shows the coomassie stain and immunoblot analysis of recombinant EBV gH/gL and gH/gL-specific IgG titers from diluted sera (1:100, 1:300 and 1:900).

FIG. 11A shows maturation of dendritic cells generated from human PBMCs (EBV seropositive individuals). From top to bottom, the samples are unstained, no VLP, 1 μl VLP, 2 μl VLP, and 4 μl VLP. FIG. 11B shows CFSE proliferation of Sample No. 18. FIG. 11C shows CFSE proliferation of Sample No. 19.

FIG. 13A shows PCR amplification of EBV gp350-gB-gp42-gL-gH from PCAGGS using primers with engineered restriction site for cloning into transfer vector (panel 1), ligation of EBV gp350-gB-gp42-gL-gH PCR fragment into pGEM transfer vector containing a mH5 promoter, multiple cloning site (MCS) and transcription termination signal (TS) (panel 1), insertion of Kanamycin resistance marker gene (KanR) and a I-SceI restriction site flanked by 50 bp gB duplicate sequence (panel 3), PCR amplification of mH-EBV gp350-gB-gp42-gL-gH-TS using primers with 50 bp MVA duplicate sequence overhangs (panel 4). PCR product is inserted into MVA-BAC via a first Red recombination utilizing the 50 bp MVA overhangs sequence, and the Kan selection marker is removed from the new MVA construct by introducing a double-strand break at the I-SceI site and followed by a second Red recombination between the 50 bp gB sequence duplication (panel 5). FIG. 13B shows MVA-BAC construct (not to scale) illustrating the five gene insertion sites: (1) Del2, (2) IGR3, (3) G1L/18R, and (4-5) Del3, going in different orientations.

DETAILED DESCRIPTION

Figure 1A:
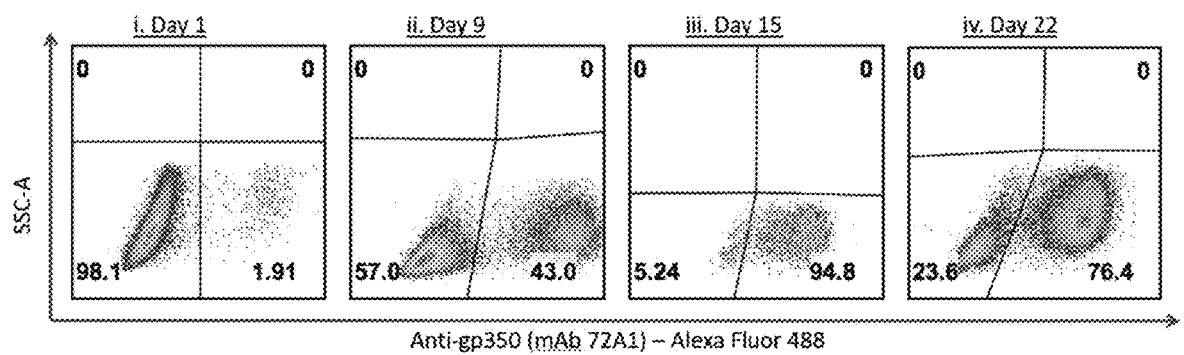
FIGS. 1A-1C show generation and flow cytometry analysis of stable cells expressing gp350-F-gB-F-gp42-WT-gL-WT-gH-F.

Expression systems, vectors, vaccines for use in preventing or treating EBV infections are provided herein. The single polyvalent EBV subunit vaccine, which is described in detail below, can stimulate both humoral (antibody) and T cell-mediated immunity, and generate both prophylactic and therapeutic antiviral responses against EBV infection and EBV-associated malignancies.

EBV uses multiple glycoproteins to initiate entry and infection of host cells, making them potential targets for a prophylactic vaccine[6]. gp350, gB, gp42, and the gH/gL complex or BMRF2/BDLF2 complex are the attachment/fusion glycoproteins that mediate EBV entry into host cells. They are expressed on the virions and in infected cells, and stimulate humoral and cellular immune responses in humans and in animal models. gp350 cellular receptor interactions initiate EBV attachment to B cells and trigger endocytosis of the virions[6]. Although this interaction enhances infection, it is not essential[7]. All clinical trials to date, which used gp350 protein as the only target protein for eliciting neutralizing antibodies have failed.[3,6-8]

Antibodies provide the first line of defense against viral infection. Neutralizing antibodies (nAbs) directed against EBV envelope glycoproteins are present in humans, may prevent neonatal infection, and are generated in response to immunization of humans[3]. However, persistent EBV infection and the limited evidence of immune selection of viral antigenic variants indicate that in vivo neutralization of EBV infection is suboptimal. Thus, it is important to develop a multivalent EBV vaccine that triggers both arms of the immune system to elicit robust humoral and cellular responses.

The ability of gB and gH/gL antibodies to neutralize infection is also well-conserved in herpes simplex virus-1, cytomegalovirus, and Kaposi sarcoma-associated herpesvirus[5]. Furthermore, gB serves as fusion machinery and gp42 and gH/gL complexes confer host cell specificity to mediate EBV entry into B cells and epithelial cells, respectively. Importantly, the gp42 protein is unique to EBV, and recombinant EBV lacking gp42 or gH does not infect either epithelial or primary B cells[11,12].

Even though certain functions of some viral protein subunits were studied, selection of appropriate viral protein subunits is very important and unpredictable for producing an effective vaccine. Although the major EBV surface glycoprotein gp350/220 (gp350) has been proposed as an important antigen, attempts over the past four decades to develop a potent gp350-based vaccine have shown limited success. In four independent phase I/II clinical trials, vaccination with vector constructs expressing gp350 or with purified recombinant non-splicing variant gp350 soluble protein did not prevent EBV infection, although acute infectious mononucleosis was reduced in young adults[3, 6-8].

Selection of an appropriate platform is also important and unpredictable. Virus-like particles (VLPs) lack the viral genome and typically assemble from viral structural proteins, forming repetitive arrays that resemble a natural virus. As disclosed herein, this platform allows inclusion of multiple select surface glycoproteins and intracellular T-cell antigens in a polyvalent vaccine.

Similar to other herpesviruses, EBV enters various cell types using multiple surface glycoproteins. Thus, the inclusion of multiple glycoproteins in the vaccine is needed to overcome the limitation of using gp350 alone. Disclosed herein is a platform to present multiple EBV surface glycoproteins (gp350, gB, gp42, or gH/gL) to elicit antibodies which can neutralize EBV infection in vivo.

The current opinion in the field is that protection against EBV not only relies on elicitation of nAbs but also induction of CD4+ and CD8+ T-cell immune responses specific to viral latent antigens (EBNA1, EBNA2, EBNA3a, EBNA3b, EBNA3c, EBNA-LP, LMP1, or LMP2). Thus, current EBV therapeutic vaccine candidates have focused on enhancing such responses[9].

EBV nuclear associated protein 1 (EBNA1) and latent membrane protein 2 (LMP2) are intracellular proteins expressed in all EBV-infected cells, including EBV-associated tumors in children and Burkitt Lymphoma tumors. EBNA1-LMP2-specific CD4+ and CD8+ T cells are frequently detected in EBV-infected individuals, and both T-cell subsets can be effective in controlling growth of EBV-immortalized cells. Thus, disclosed herein is the inclusion of EBNA1 and LMP2 as components of a polyvalent vaccine which can trigger an effective T cell-mediated therapeutic response.

The major limitations of vaccines in pre-clinical and clinical trials to date are that none of the vaccines has created sterile immunity (i.e., complete blockage of viral infection) and that most of the strategies only target one arm of the immune system, humoral or T cell-mediated. Even in cases where both arms of the immune system have been targeted in a single vaccine, such as with the use of EBV DNA packaging mutants[18, 19], the vaccine candidates have met with limited immunogenicity, safety concerns, and failure to induce robust CD8+ T-cell responses[4].

Thus, disclosed herein is a novel single prophylactic and therapeutic polyvalent VLP vaccine comprising two or more EBV envelope glycoproteins and one or more T cell antigens. In some embodiments, the VLP vaccine comprises two, three, four, five or more EBV envelope glycoproteins. In some embodiments, the VLP vaccine comprises two or more T cell antigens. In some embodiments, the EBV envelope glycoproteins include gp350, gB, gp42, gH, gL, and any other known EBV envelope glycoproteins such as gM, gN, BMRF2, BDLF2, BDLF3, BILF2, BILF1, and BARF1. In some embodiments, the T cell antigens include EBNA1 and LMP2 or any other EBV neoantigens. In some embodiments, the VLP vaccine can include other EBV neoantigens such as LMP2, EBNA3a-c etc. In some embodiments, the VLP vaccine comprises seven selected proteins including five EBV envelope glycoproteins: gp350, gB, gp42, gH, and gL, and two T cell antigens: EBNA1, and LMP2. In some embodiments, in addition to the EBV envelope glycoproteins and T cell antigens, the VLP further comprises NDV structural proteins including fusion (F), matrix (M), and nucleocapsid (NP). In some embodiments, the VLP vaccine further comprises one or more adjuvants.

In some embodiments, disclosed herein is a single vector co-expressing two or more EBV envelope glycoproteins including gp350, gB, gp42, gH, and gL, with each glycoprotein separated from another glycoprotein by 2A sequence. For example, multicistronic 2A sequence is used in a pCAGGS-gp350-F-gB-F-gp42-WT-gL-WT-gH-F vector. The 2A sequence can be, for example, 15 amino acids, 16 amino acids, 17 amino acids, 18 amino acids, 19 amino acids, 20 amino acids, 21 amino acids, 22 amino acids, 23 amino acids, 24 amino acids, or 25 amino acids in length. In some embodiments, a sequence of GAAGAGA (SEQ ID NO:1) is used to generate fusion protein between EBNA1 and LMP2 antigens, e.g., NP-EBNA1-LMP2. In some embodiments, a full-length NP sequence or a 26-amino acid of NP sequence is used to deliver or package EBNA1 and LMP2 into the VLPs. In some embodiments, wild-type EBNA1 is used or the EBNA1 Gly-Ala rich regions are deleted before packaging.

The amino acid sequence of the full-length NP is as follows (SEQ ID NO:2):

```
MSSVFDEYEQLLAAQTRPNGAHGGGEKGSTLKVEVPVFTLNSDDPEDRWNFVVFCLRIAV    60

SEDANKPLRQGALISLLCSHSQVMRNHVALAGKQNEATLAVLEIDGFTNSVPQFNNTSGV   120

SEERAQRFMMIAGSLPRACSNGTPFITAGVEDDAPEDIIDTLERILSIQAQVWVTVAKAM   180

TAYETADESETRRINKYMQQGRVQKKYILHPVCRSAIQLTIRQSLAVRIFLVSELKRGRN   240

HAGGSSTYYNLVGDVDSYIRNTGLTAFFLTLKYGINTKTSALALSSLAGDIQKMKQLMRL   300

YRMKGDNAPYMTLLGDSDQMSFAPAEYAQLYSFAMAMASVLDKGTGKYQFARDFMSTSFW   360

RLGVEYAQAQGSSINEDMAAELKLTPAARRGLAAAAQRVSEETSSMDIPTQQAGVLTGLS   420

DGGPQAPQGGSNRSQGRPDAGDGETQFLDLMRAVANSMREAPNSVQSTTQPEPPPTPGPS   480

QDNDTDWGY                                                      489
```

In some embodiments, the amino acid sequence of the 26 AA fragment of the NP is SVQSTTQPEPPPTPGP-SQDNDTDWGY (SEQ ID NO:3).

In some embodiments, disclosed herein is a method of producing Epstein-Barr virus-like particles with polycistronic vector using one or more 2A sequences in a pCAGGS-gp350-F-gB-F-gp42-WT-gL-WT-gH-F vector. The 2A sequence can be, for example, 15 amino acids, 16 amino acids, 17 amino acids, 18 amino acids, 19 amino acids, 20 amino acids, 21 amino acids, 22 amino acids, 23 amino acids, 24 amino acids, or 25 amino acids in length. The method can further entail generating fusion protein between truncated EBNA1 and LMP2 or any other two or more EBV latent proteins using a sequence of GAAGAGA (SEQ ID NO:1) to form a fusion of NP-EBNA1-LMP2 or NP fused to other one or more latent proteins. In some embodiments, a full-length NP sequence or a 26-amino acid of NP sequence is used to deliver or package EBV latent proteins into the VLPs. In some embodiments, wild-type EBNA1 is used or the EBNA1 Gly-Ala rich regions are deleted before packaging for MHC I presentation.

As demonstrated in the working examples, subunit VLPs incorporating EBV antigens were efficiently produced in Chinese hamster ovary cells, a U.S. Food and Drug Administration-approved vehicle for most biologics production, and stimulate both humoral and T cell-mediated immune responses in vitro and in vivo. The polyvalent gp350-gB-gp42-gH/gL-EBNA1-LMP2 VLPs (EB VLPs) can generate robust protective anti-gp350-gB-gp42-gH/gL neutralizing antibodies (nAbs) and EBNA1-LMP2-specific T-cell responses to EBV infection.

In some embodiments disclosed herein, the EBV envelope glycoproteins can be expressed by any suitable expression vectors including plasmid vectors and viral vectors. In some embodiments, modified Ankara vaccinia vector, adeno-associated viruses, or baculovirus can be used for co-expressing two or more EBV envelope glycoproteins. The individual glycoproteins can be linked by cleavage sequences such that the co-expressed glycoproteins can be self-cleaved and self-assembled into two or more glycoprotein complexes.

In some embodiments, the expression systems or vectors described herein include two or more expression cassettes, each of which includes a single promoter and a sequence that encodes two or more EBV envelope glycoproteins. As a result, the two or more EBV envelope glycoproteins are co-expressed simultaneously, i.e., under control of a single promoter, obviating the need for multiple promoters or vectors. In certain embodiments, each expression cassette includes two, three, four, five, or even higher numbers of EBV glycoproteins, the expression of which are under control of a single promoter. In some embodiments, a vector may include more than one such expression cassette.

In some embodiments, internal ribosome entry sites (IRES) can be introduced in between nucleic acid sequences encoding two or more EBV envelope glycoproteins that are co-expressed, flanking the sequences encoding the two or more glycoproteins. Although IRES can be used to link the expression of multiple genes under a single promoter, the use of multiple IRES sequences might be limited by size constraints, instability due to its relatively larger size comparing to 2A signal sequences, and/or difference in expression levels between the genes located before and after an IRES. In some embodiments, 2A signal sequences that encode for the 2A peptide of food-and-mouth disease virus (F2A), equine rhinitis A virus (E2A), porcine teschovirus-1 (P2A), Thoseaasigna virus (T2A), cytoplasmic polyhedrosis virus (BmCPV 2A), or flacherie virus (BmIFV 2A) can be used to link multiple genes under a single promoter. 2A signal sequences have been found in picornaviruses, insect viruses and type C rotaviruses. In some embodiments, a self-cleavage 2A peptide-derived sequence from Picornaviruses[12] is used to co-express EBV envelope glycoproteins including gp350, gB, gp42, gH and gL in native form on the surface of a VLP. Bicistronic or multicistronic expression vectors can be used to express more than one gene product within a cell. Various suitable eukaryotic cell promoters can be used, including but not limited to, immediate-early I promoter of human CMV or the chicken beta actin promoter, promoters of vaccinia virus (mH5, pSyn, P11, p7.5), etc.

Additionally, a furin cleavage site preceding the 2A signal sequences can be incorporated to remove the 2A peptides following self-processing of the 2A-linked polyproteins. Furin is an enzyme that occurs in the Golgi apparatus and cleaves at very short signal peptides such as KKKR (SEQ ID NO:4) or RKKR (SEQ ID NO:5) motif. Furin cleavage contributes to protein processing and maturation. These short signal peptides can be added to the N-terminus of the 18-22 amino acid long 2A skipping signals so that they are removed following 2A-mediated processing of the EBV envelope glycoproteins, except for one or two remaining amino acids. The resultant product can be even more "native." Although it is preferred that the 2A-linked glycoproteins are expressed all from one vector through the use of one or more expression cassettes, it is also possible to express the 2A-linked subunits from two or more separate vectors.

By exploiting the ribosomal skipping mechanism conferred by 2A peptides, an approach of co-expressing the EBV envelope glycoproteins as only one or two self-processing polyproteins is disclosed herein. The 2A ribosomal skipping system is widely-used to express multi-protein complexes due to the relative small sizes of 2A peptides (18-22 amino acids) and because it allows stoichiometric expression of the individual 2A-linked subunits. In some embodiments, P2A-linked DNA sequences of two or more EBV envelope glycoproteins are co-expressed and efficiently cleaved and transported to the cell surface. In some embodiments, the DNA sequences encoding the EBV envelope glycoproteins are codon-optimized. In some embodiments, the co-expressed EBV envelope glycoproteins are self-assembled into surface complexes, including gp42-gH/gL and gB-gH/gL.

According to the embodiments described herein, an immunization regimen is provided. The immunization regimen includes VLPs comprising two or more EBV envelope glycoproteins and one or more T cell antigens. The immunization regimen may be administered via prime/boost homologous (e.g. using only the same vaccine type) or heterologous (e.g. using different vaccine types) vaccination. The immunization regimen may be administered in a dose vaccination schedule involving two or more immunizations, which may be administered 2 weeks to 6 months apart. Other suitable immunization schedules or regimens that are known in the art may be used according to the embodiments described herein by those skilled in the art.

According to some embodiments, the nucleic acid sequences encoding two or more EBV envelop glycoproteins are assembled into a single vector, with a linking sequence inserted between the nucleic acid sequences encoding two or more subunits. For example, the EBV envelope glycoproteins may be linked through linking sequences such as internal ribosome entry sites (IRES), derived from a number of different RNA viruses that are well known in the art and sequences encoding 2A peptides, to link all or some of the EBV envelop glycoproteins. The 2A signal sequence encoding a 2A peptide of foot-and-mouth disease virus (F2A), a 2A peptide of equine rhinitis A virus (E2A), a 2A peptide of porcine teschovirus-1 (P2A), a 2A peptide of cytoplasmic polyhedrosis virus (BmCPV 2A), a 2A peptide of flacherie virus (BmIFV 2A), or a 2A peptide of Thosea asigna virus (T2A), can be used.

The vaccine composition as described herein may comprise a therapeutically effective amount of a VLP as described herein, and may further comprise a pharmaceutically acceptable carrier according to a standard method. Examples of acceptable carriers include physiologically acceptable solutions, such as sterile saline and sterile buffered saline.

In some embodiments, the vaccine or pharmaceutical composition may be used in combination with a pharmaceutically effective amount of an adjuvant to enhance the anti-EBV effects. Any immunologic adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Alum, Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GM-CSF and IL-12, chemokines such as MIP 1-α and RANTES, activating cell surface ligands such as CD40L, N-acetylmuramine-L-alanyl-D-isoglutamine (MDP), and thymosin α1. The amount of adjuvant used can be suitably selected according to the degree of symptoms, such as softening of the skin, pain, erythema, fever, headache, and muscular pain, which might be expressed as part of the immune response in humans or animals after the administration of this type of vaccine.

In further embodiments, use of various other adjuvants, drugs or additives with the vaccine of the invention, as discussed above, may enhance the therapeutic effect achieved by the administration of the vaccine or pharmaceutical composition. The pharmaceutically acceptable carrier may contain a trace amount of additives, such as substances that enhance the isotonicity and chemical stability. Such additives should be non-toxic to a human or other mammalian subject in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); antibiotics; and PEG.

The vaccine or pharmaceutical composition containing a VLP described herein may be stored as an aqueous solution or a lyophilized product in a unit or multiple dose container such as a sealed ampoule or a vial.

The expression systems, vectors and vaccines described herein may be used to treat or prevent any EBV infection or conditions associated with EBV infection such as EBV+ lymphomas, carcinomas, PTLDs, multiple sclerosis among other diseases.

As used herein, the term "subject" is an animal. In some embodiments, the subject is a mammal. In some embodiments, the subject is human.

The term "an effective amount" as used herein refers to an amount of a composition that produces a desired effect. For example, a population of cells may be infected with an effective amount of a viral vector to study its effect in vitro (e.g., cell culture) or to produce a desired therapeutic effect ex vivo or in vitro. An effective amount of a composition may be used to produce a prophylactic or therapeutic effect in a subject, such as preventing or treating a target condition, alleviating symptoms associated with the condition, or producing a desired physiological effect. In such a case, the effective amount of a composition is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the composition (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the composition is administered alone or in combination with another composition, drug, therapy or other therapeutic method or modality. One skilled in the clinical and pharmacological arts will be able to determine an effective amount or therapeutically effective amount through routine experimentation, namely by monitoring a cell's or subject's response to administration of a composition and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, PA, 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In some embodiments, the vaccine or pharmaceutical composition described herein may be used in combination with other known pharmaceutical products, such as immune response-promoting peptides and antibacterial agents (synthetic antibacterial agents). The vaccine or pharmaceutical composition may further comprise other drugs and additives. Examples of drugs or additives that may be used in conjunction with a vaccine or pharmaceutical composition described herein include drugs that aid intracellular uptake of the composition or vaccine disclosed herein, liposome and other drugs and/or additives that facilitate transfection, (e.g., fluorocarbon emulsifiers, cochleates, tubules, golden particles, biodegradable microspheres, and cationic polymers).

In some embodiments, the vaccine composition or pharmaceutical composition described herein may be administered by directly injecting a VLP suspension prepared by suspending the VLP in PBS (phosphate buffered saline) or saline into a local site, by nasal or respiratory inhalation, or by intravascular (i.v.) (e.g., intra-arterial, intravenous, and portal venous), subcutaneous (s.c.), intracutaneous (i.c.), intradermal (i.d.), or intraperitoneal (i.p.) administration. The vaccine or pharmaceutical composition of the present invention may be administered more than once. More specifically, after the initial administration, one or more additional vaccinations may be given as a booster. One or more booster administrations can enhance the desired effect. After the administration of the vaccine or pharmaceutical composition, booster immunization with a pharmaceutical composition containing the VLP as described herein may be performed.

The following examples are intended to illustrate various embodiments of the invention. As such, the specific embodiments discussed are not to be constructed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Construction of Polycistronic Plasmid, Generation and Flow Cytometry Analysis of Stable Cells Expressing Gp350-F-gB-F-Gp42-WT-gL-WT-gH-F Chimeric fragments of gp350 (1-864), gB (1-735), and gH (1-679) were constructed by fusing the ectodomain (ED) of the individual viral proteins to the Newcastle disease virus fusion protein (NDV-F) transmembrane (TM) and cytoplasmic (CT) domains. These chimeric fragments, along with gp42 wild-type (1-223) and gL wild type (1-140) were encoded as a single transcript (gp350-F-gB-F-gp42-WT-gL-WT-gH-F) within a modified pCAGGS vector. Each of the viral proteins was separated by a short unique 2A peptide sequences, which acts as a cleavage signal peptide during processing.

CHO cells were co-transfected with polycistronic pCAGGS-gp350-F-gB-F-gp42-WT-gL-WT-gH-F and pCl-puro plasmids. Forty-eight hours post-transfection, cells were cultured in media containing 10 μg/ml of puromycin. Selected cells were stained with anti-gp350 monoclonal antibody (mAb) 72A1 at a concentration of 1:200, followed by staining with secondary antibody, goat anti-mouse IgG conjugated to Alexa Fluor 488 (1:1000). Stained cells were washed three times with phosphate buffer saline, sorted using flow cytometry and positive cells expanded under selection of puromycin and further sorted four times as indicated in FIG. 1A, panels i-iv. Stable CHO cells reached approximately 95% positivity by the third sort (FIG. 1A, panel iii), and subsequently the concentration of puromycin was reduced to 5 μg/ml (FIG. 1A, panel iv).

Figure 1B:
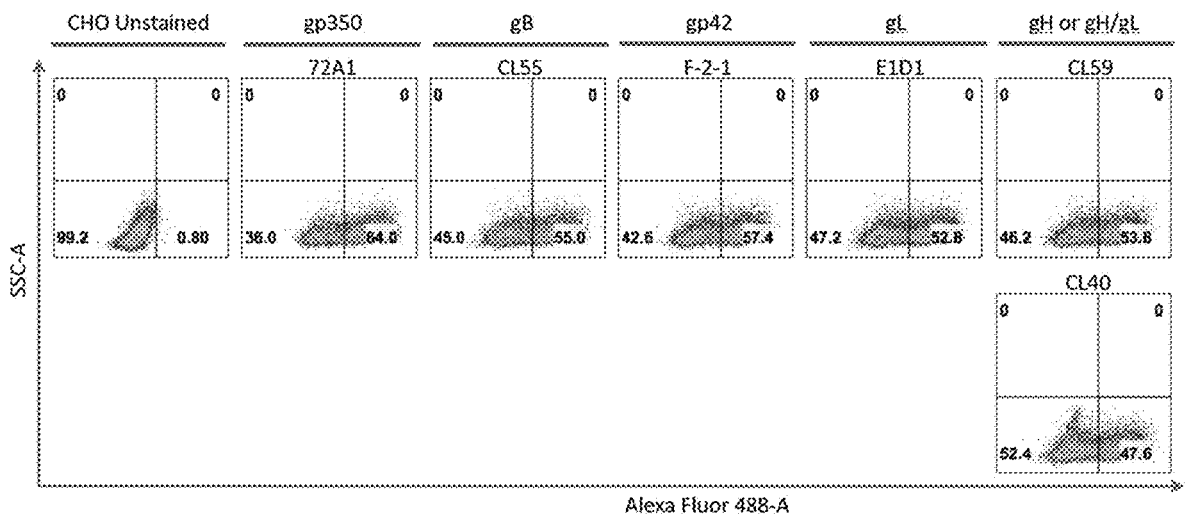

As shown in FIG. 1B, FACS analysis of cells maintained in 5 μg/ml of puromycin showed a decrease in the percent of positive cells when stained with mAb-72A1, anti-gB mAb (CL55), anti-gp42 mAb (F-2-1), anti-gL mAb (E1D1), anti-gH mAb (CL59), or anti-gH/gL mAb (CL40) at concentrations of 1:200, followed by staining with secondary antibody, goat anti-mouse IgG conjugated to Alexa Fluor 488 (1:1000) and analyzed by flow cytometry.

Figure 1C:
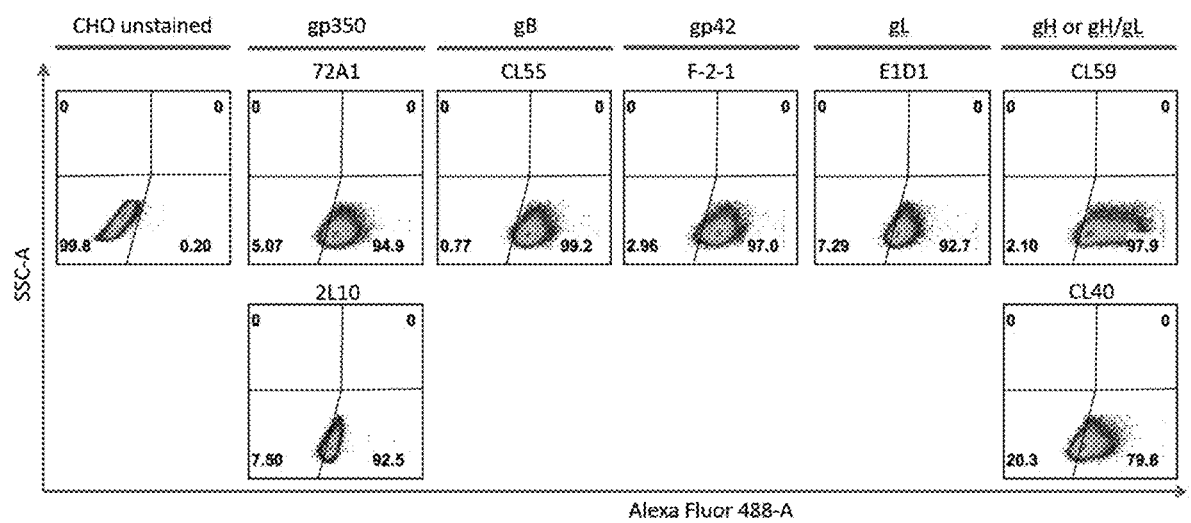

Stable CHO cells expressing all the five EBV glycoproteins were enriched, stained, and analyzed as described above. During this period another anti-gp350 mAb 2L10 was also used. The transfected cells were compared to unstained cells and cells stained with the isotype control alone (data not shown). As shown in FIG. 1C, stable CHO cells maintained in 10 μg/ml of puromycin expressed >90 percent positivity of all the five glycoproteins incorporated. Anti-gp350 mAb (72A1, 2L10) mAbs were purchased from Millipore; mAbs E1D1, CL55, F-2-1, CL59, CL40 were gifts of L. Hutt-Fletcher (Louisiana State University, Shreveport).

Example 2: EB VLPs in Eliciting Immune Responses in Wild Type BALB/Mice

Construction of gp350-gB-gp42-gH/gL-EBNA1-LMP2 VLP plasmids: To develop EB VLPs, pCAGGS-NDV M, and a fusion protein encoding for a truncated EBNA1 [amino acids (aa) 325-641], and full-length LMP2 fused to 26aa of NDV NP (aa 474-489) were synthesized. Full-length NDV NP was used previously to package EBNA1 and LMP2 inside gH/gL and gB VLPs, respectivelyl[7]. It was recently shown that >15 aa of the NP sequence of paramyxoviruses is sufficient to deliver foreign proteins inside a VLP21. Thus, the NP fragment (26aa NDV NP) was truncated to significantly increase the efficiency of packaging EBNA1-LMP2 into the EB VLP. Production and characterization of EB-VLPs are illustrated in FIG. 2.

To construct the gp350-gB-gp42-gH/gL glycoproteins, a chimeric fragment encoding a polycistronic gp350-F-gB-F-gp42-gL-gH-F was synthesized, in which the ectodomains of g350, gB, and gH were fused to the NDV F transmembrane/cytoplasmic domains[17]. To enable expression and interaction between gH/gL and gp42 or gB as native complexes gp42-gH/gL or gB-gH/gL, unique amino acid 2A linker sequences (18 aa) were interspersed between individual gene cDNAs. This provides a cleavage site that allows gp350, gB, gp42, gL, and gH to be expressed at similar ratios from a single transcript and be independently released. The synthesized chimera was cloned into a mammalian expression vector (pCAGGS) and verified sequence fidelity. cDNAs of full-length gp35022, NDV M, gB, gp42, gH/gL, gp42-gH/gL, gB-gH/gL, LMP2, and EBNA1 were synthesized and individually cloned into pCAGGS as controls for characterization studies.

As shown in FIG. 2A, the plasmid encoding for five EBV glycoproteins gp350-F-2A-gB-F-2A-gp42-WT-2A-gL-WT-2A-gH-F from a single transcript was transfected into CHO cells or human embryonic kidney 293 cells along with a plasmid containing a puromycin resistance gene to generate stable cells. The transfected cells were cultured in the presence of 2-10 μg/ml of puromycin. Surviving cell colonies were expanded, stained with anti-gp350 (72A1) or anti-gH/gL (E1D1) and sorted twice by flow cytometry (FC) to enrich positive stable cells. To generate VLPs, stable cells expressing >80% of all glycoproteins by FC were co-transfected with pCAGGS-NDV-M and full length NP plasmids or NDV-M and 26aa NP-EBNA1-LMP2 plasmids (transiently or stably, see sucrose density gradient purified VLPs) indicating that use of 26aaNP-EBNA1-LMP2 does not affect efficiency of production. Representative stable cells producing VLPs stained with primary antibodies (1:200) 72A1 or E1D1 for 30 min, followed by staining with goat anti-mouse IgG-Alexa Fluor 488 (1:500) for 30 m. Cells were washed twice and analyzed by FC. The transfected cells were compared to unstained cells and cells stained with the isotype control alone as shown in FIG. 2B. Cells were also stained with anti-gB (CL55), anti-gH or gH/gL (CL59) and anti-gp42 (F-2-1) (FIG. 1).

Figure 2A:
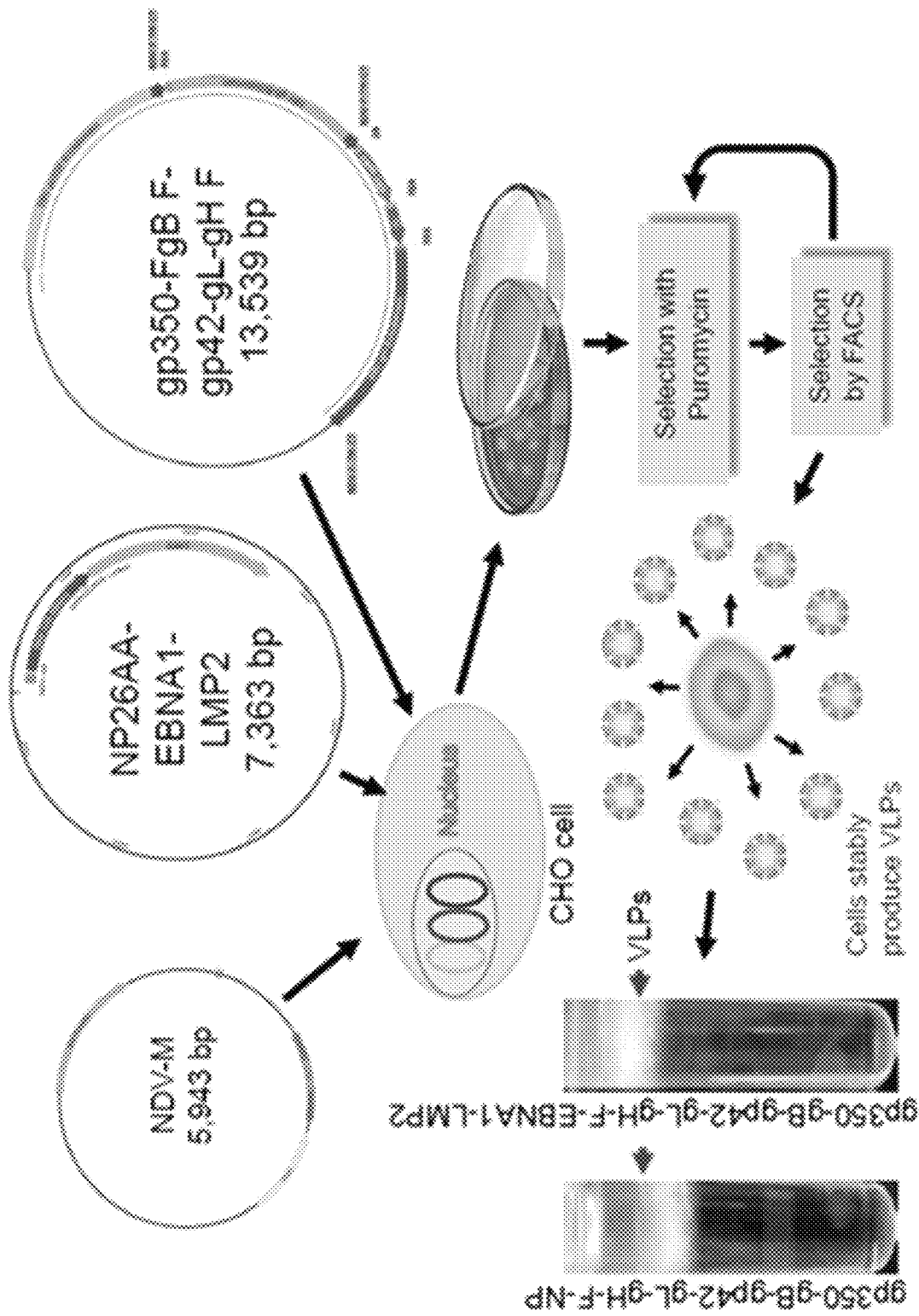
Figure 2B:
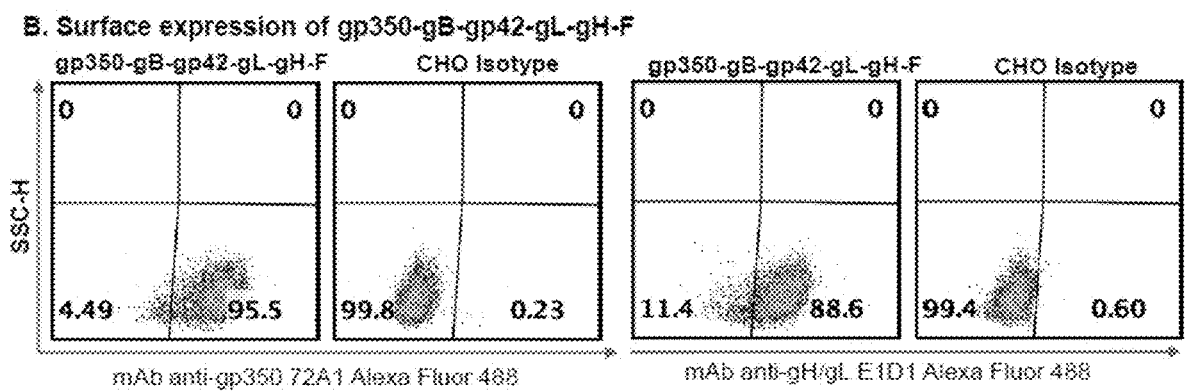
Figure 2C:
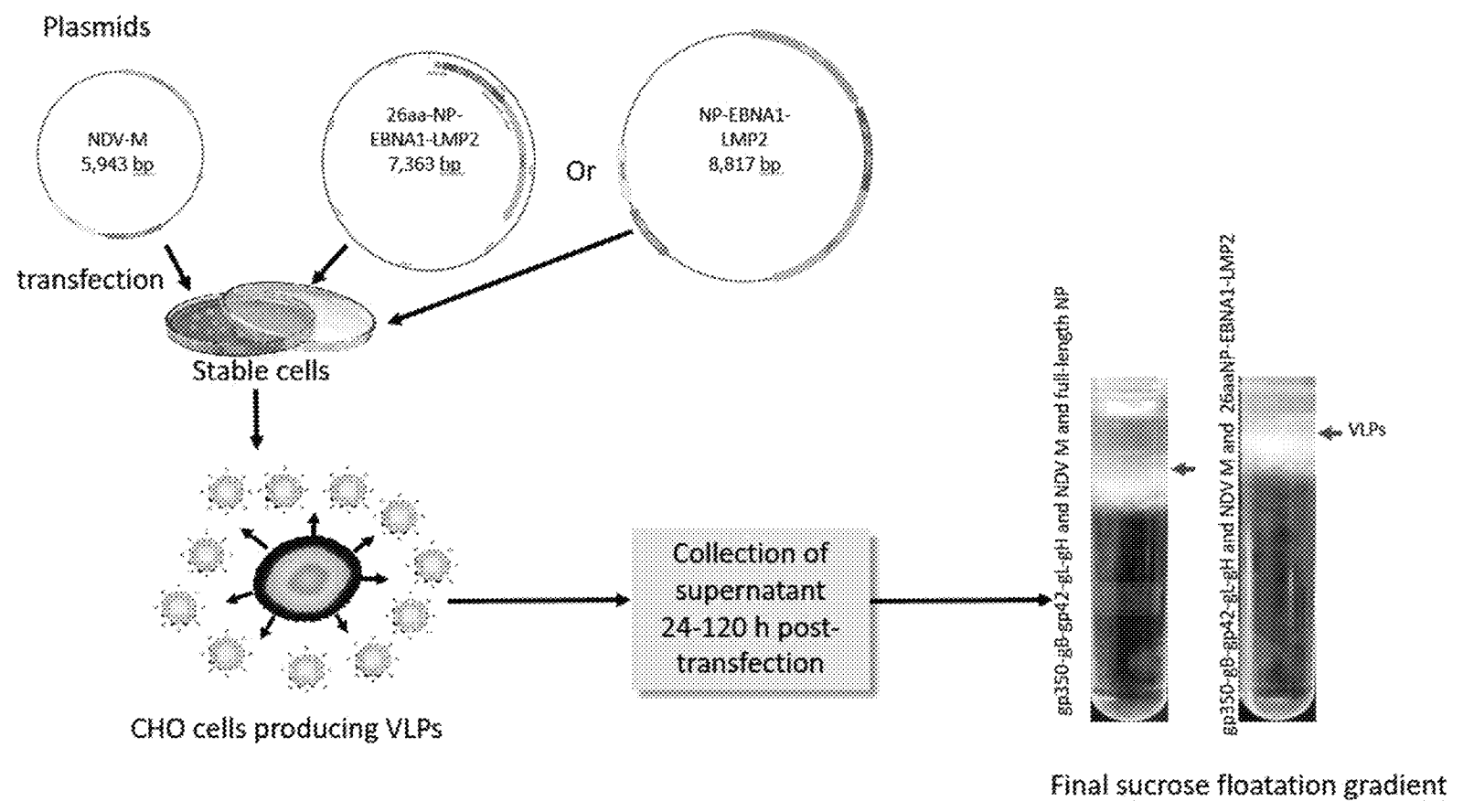

As shown in FIG. 2C, stable CHO cells expressing glycoproteins gp350, gB, gp42-WT, gL-WT and gH from a single transcript were expanded into 100 T175 flasks and cells transiently co-transfected with plasmids encoding for pCAGGS-NDV-matrix (NDV-M) and full-length NP plasmids or pCAGGS-NDV-M and plasmid encoding for 26 amino acids of NP (463-489) fused to EBNA1 (326-641) and LMP2 (1-501) (26aaNP-EBNA1-LMP2). Supernatant from transfected cells were collected every 24 hours for 5 days and EB VLPs pelleted and purified through sucrose density gradient.

Figure 3A:
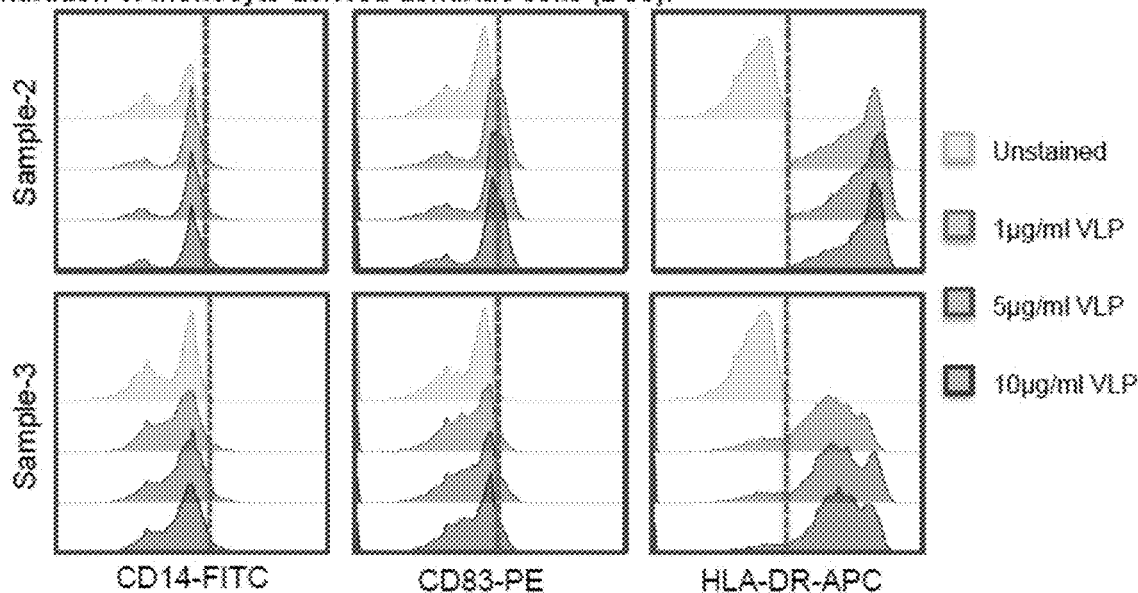
FIGS. 3A and 3B show assessment of dendritic cells maturation and stimulation of CD3 T cells.
Figure 3B:
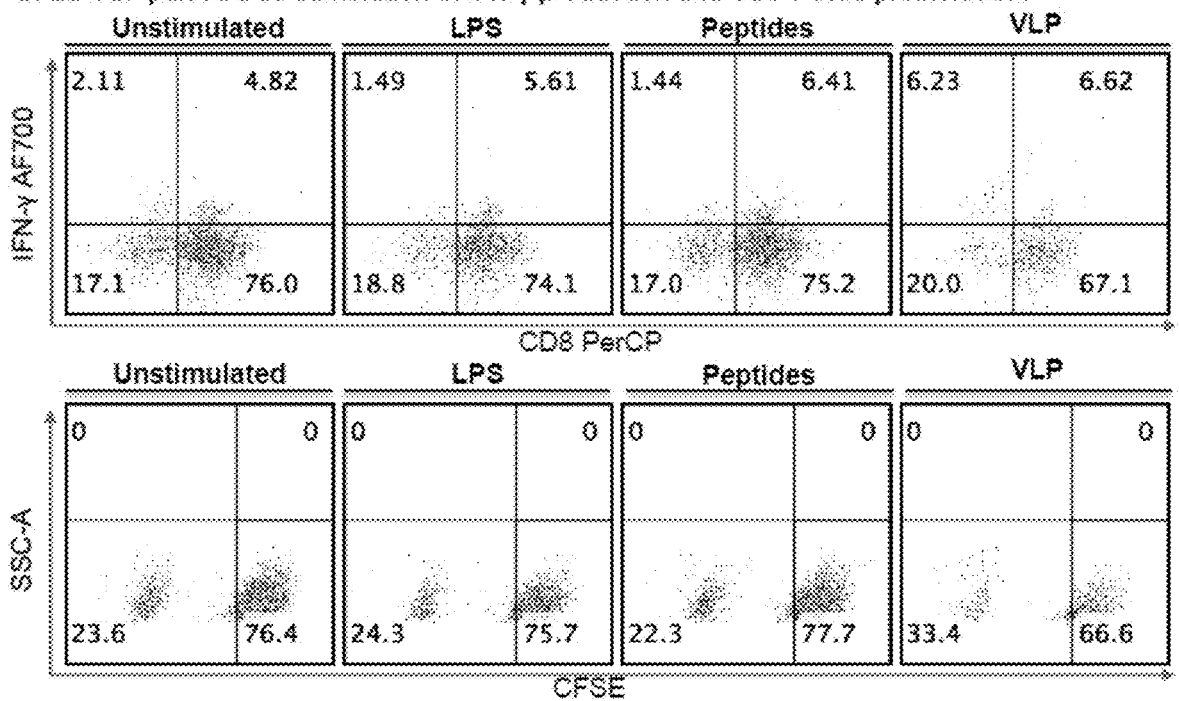
Figure 4:
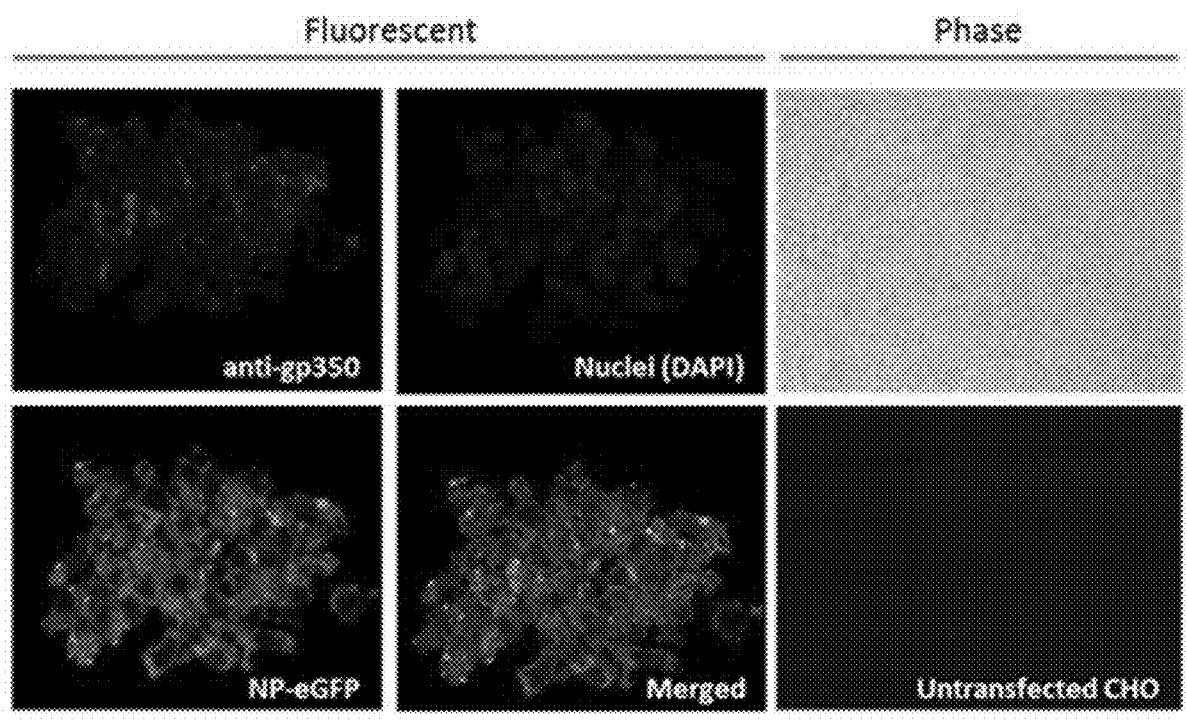
FIG. 4 shows characterization of gp350 EB VLPs and generation of stable CHO-gp350 cells. After the tenth passage, stable CHO-gp350-eGFP cells were stained with 72A1 and AF594-coupled secondary antibody (red). Expression of eGFP was detected using fluorescence detector AF488 (green). DAPI was used for nuclear staining. Sequential confocal images showed that stable CHO cells expressed both surface gp350 and intracellular eGFP, whereas no gp350 protein was detected in untransfected CHO cells (negative control). Visualization of 3D merged images confirmed the expression of gp350 and eGFP proteins on the cell surface and intracellularly, respectively.

Dendritic cells (DCs) were generated from monocytes isolated from human PBMC samples. Monocytes were maintained in culture with 100 ng/ml GM-CSF and 25 ng/ml IL-4 for 7 days to induce differentiation into DCs as shown in FIG. 3A. Differentiated DCs were stained with anti-CD14 (FITC), anti-CD83 (PE), and anti-HLA-DR (APC) and analyzed by flow cytometry before being co-cultured with autologous purified T-cells. DCs pulsed with EB VLPs were co-cultured with autologous T-cells labeled with CFSE (TC to DC ration of 60:1). On Day 7 T-cells were re-stimulated with either LPS (100 ng/ml), a pool of 25 EBV-specific peptides (50 ng/ml per peptide), or DCs freshly pulsed with EB VLPs (2.5 µl). Cultures were analyzed after 24h for CD8 expression (PerCP), CFSE, and IFN-γ production (AF-700). Brefeldin A was included in the cultures for the final 5 hours before analysis to block cytokines release. EB VLPs stimulated CD8 T cell proliferation were compared to unstimulated cells or cells stimulated with LPS or EBV peptides, as shown in FIG. 3B.

Stable CHO-gp350-gB-gp42-gH/gL cells were co-transfected with equal amounts of pCAGGS-26aa NDV NP-EBNA1-LMP2 and pCAGGS-NDV M, as well as pCI-neo plasmid to allow selection of stable cells with both puromycin and neomycin. Upon selection with both antibiotics, five clones were selected, amplified, and single-cell sorted (using antibodies described above) into 96 well-plates containing selection media (puromycin and neomycin). The sorted cells were expanded from the 96-well plate to T175 flasks and supernatant from stable cells was collected between 24-96 h, and EB VLPs were purified as described[22]. To confirm production of gp 350, gB, gp42, gH/gL, EBNA1, LMP2, and NDV components, the purified VLPs can be analyzed as described[17].

Immunization of BALB/c mice to generate nAbs: Five groups (n=5/treatment) of 6-8-week-old BALB/c wild-type mice or New Zealand white rabbits can be immunized intraperitoneally three times (Days 0, 29, and 54) with 12.5 µg, 25 µg or 50 µg of purified EB VLPs in 0.5 ml of TNE buffer adsorbed to aluminum hydroxide (alum adjuvant used to improve immunogenicity; 0.25 µg alum/µg protein). Purified UV-inactivated EBV or TNE adsorbed to alum can serve as positive/negative controls, respectively. To assess short-, mid-, and long-term immunogenic nAb responses, mice can be tail-vein bled to obtain serum at two-week intervals after primary immunization, until sacrifice at Day 97.

gp350-gB-gp42-gH/gL-specific antibody titer and neutralization assay: ELISA is used to assess and compare antibody titers against EBV glycoproteins included in the vaccine in sera collected from mice, using soluble proteins gp350, gB, gH/gL, or gp42-gH/gL (Immune Tech) or purified EBV lysate as binding targets. Sera can be used to conduct neutralization assays against EBV-eGFP produced in either B cells (B95-8) or epithelial cells (AGS) in an in vitro system using different cell lines and primary B cells as described[22]. FC is used to determine percent of EBV-eGFP+ cells. Sera from TNE-immunized animals can serve as negative controls.

Statistical analysis: Using 5 mice/dose, the minimum observed neutralizing activity serves as a simple lower 97% confidence limit on the median, so ≥70% neutralizing activity in all 5 mice at the highest dose is observed, it is concluded that the median neutralizing activity is significantly greater than 70%, which is regarded as a promising level of neutralization. Neutralizing activity is reported as median and range for the five mice in each group, the range serving as a 95% confidence interval. Isotonic regression (pooling non-significant order violators) is used to smooth medians if they do not increase with dose. Antibodies titers can be summarized using a similar approach. The main comparisons of interest are between the highest dose and the UV-EBV control. Preliminary data on antibody titers gave 0.47 as the coefficient of variation (8 antigens, root mean square SD of log titers). With 5 mice/dose, this provides 80% power to detect a difference of 0.95 on the natural log scale, i.e., an antibody titer ratio of 2.6, or its reciprocal 0.38. The comparisons are presented as the ratio of geometric means, with a 95% confidence interval.

Example 3: Determining the Efficacy of the EB VLP Vaccine in a Humanized Mouse Model and In Vitro In this example, a mouse model harboring a functional human immune system can be used. To replicate human vaccine responses in vitro, where VLP-pulsed human peripheral blood mononuclear cells (PBMCs) can be used as antigen-presenting cells to expand EBV-specific CD4+ and CD8+ T cells[18].

Immunization of humanized mice to generate nAbs: huNSG-BLT mice can be used to test the ability of the EB VLP to block EBV primary infection of human B cells and elicit EBV-specific T-cell responses in vivo. The mice are immunized and antibody titer is determined as described in Example 2.

Viral challenge in huNSG-BLT mice: To determine vaccine efficacy, immunized mice are challenged with ~1×10³ TD$_{50}$ (50% transforming dose) of EBV-eGFP intravenously through the tail vein three weeks after final immunization. The blood is collected at 0, 6, 24, 48, 96, and 120 h post-inoculation. FC is used to quantify the number of infected B cells in vivo (EBV-eGFP+). To assess EBV replication, at various time points, PBMCs are isolated, viral RNA/DNA is extracted, and RT-PCR and qPCR are used to detect and quantify viral DNA, using specific primers for EBV biomarkers such as EBV-encoded RNA, EBNA1, LMP1, or LMP2.

Quantification and quality of T-cell responses: To enumerate the number of EBNA1-LMP2 or any other EBV antigen-specific CD4+ and CD8+ T cells, autologous T cells co-cultured with pulsed DCs are stained using T-cell markers CD3/CD4/CD8, and EBNA1-LMP2- or any other EBV antigen-specific pentamers (PeproTech). FC staining can be used for extracellular markers CD3/pentamer-positive populations by CD4+ vs. CD8+ status, CD137+, and cytokines expressions.

Statistical Analysis: Collecting >100,000 events can provide statistical differences by t-test. A quantitative analysis by FC can be performed to measure the in vitro expansion of EB VLP-specific T cells from purified human dendritic cells pulsed with purified EB VLPs.

Figure 5A:
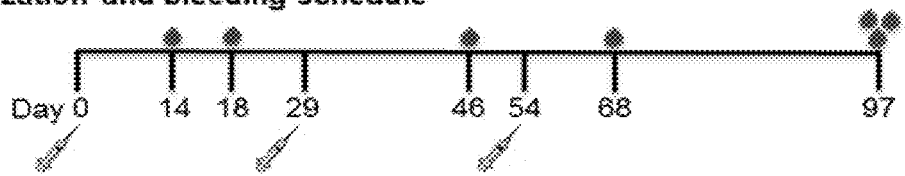
FIGS. 5A-5C show immunization schedule and generation of neutralizing antibodies in immunized BALB/c mice.
Figure 5B:
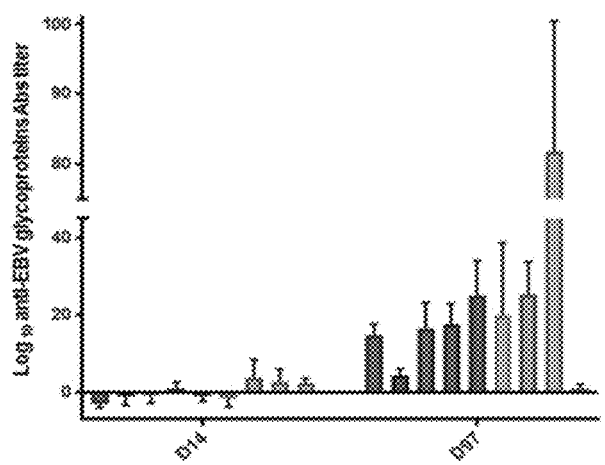
Figure 5C:
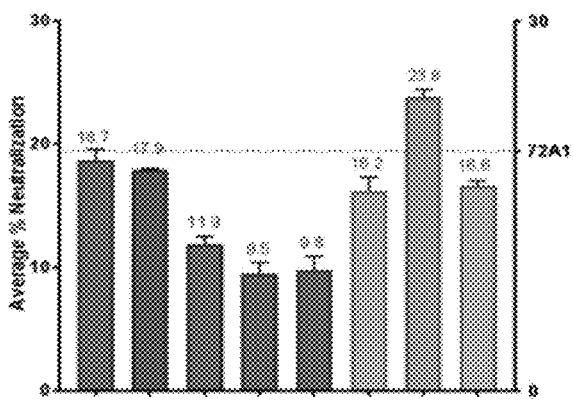

To assess the ability of sera from EB VLP-immunized mice to neutralize infection in vitro, pooled sera collected at Day 97 were used in neutralization assays in HEK-293 epithelial and Raji B-cell lines, which are susceptible to AGS-EBV-eGFP, as evidenced by eGFP+ cells[22]. Virus titer and percent of eGFP+ Raji cells were determined by flow cytometry (FC) as described[22], and neutralization titer was defined as 50% inhibition of infection, compared to control sera from EBV-seronegative animals. When 5 µl of AGS-EBV-eGFP virus was pre-incubated with serially diluted sera (1:1, 1:2.5, and 1:5) from TNE-immunized mice (negative control), fluorescence dropped from 50% (virus alone) to 40% and was used to normalize percent infection. In contrast, serially diluted sera from mice immunized with EB VLPs or UV-inactivated EBV neutralized infection in a dose-dependent manner (FIG. 5C). Purified anti-gp350 mAb 72A1 (5 µg/ml), known to block EBV infection[24], served as positive control (dotted line). Mice immunized with a combination of all three EB VLPs (gp350, gB-LMP2, and gH/gL-EBNA1) was the most effective in neutralizing infection (23.8%), followed by gp350 (18.7%), gB (17.9%), or UV-inactivated EBV (16.6%). Thus, only sera from mice immunized with a mixture of all three VLPs neutralized over 50% of EBV infection (relative to negative control) in vitro; this was more effective than gp350 (p<0.012) or all other immunogens (p<0.0001). Similar trends were observed in HEK293 cells (data not shown). These results suggest that an effective EBV prophylactic vaccine requires multiple gps.

Example 4: Immunoblot Analysis of Transfected Cells and Purified EB VLPs

Untransfected CHO cells, transfected cells, purified EB VLPs (gp350-gB-gp42-gL-gH or gp350-gB-gp42-gL-gH-EBNA1-LMP2) and purified EBV were lysed, run on a 4-12% SDS polyacrylamide gel, and analyzed using immunoblot. Briefly, proteins were transferred onto immunoblot membrane, blocked with 3% BSA for one hour and followed by primary and secondary antibody staining.

Figure 6A:
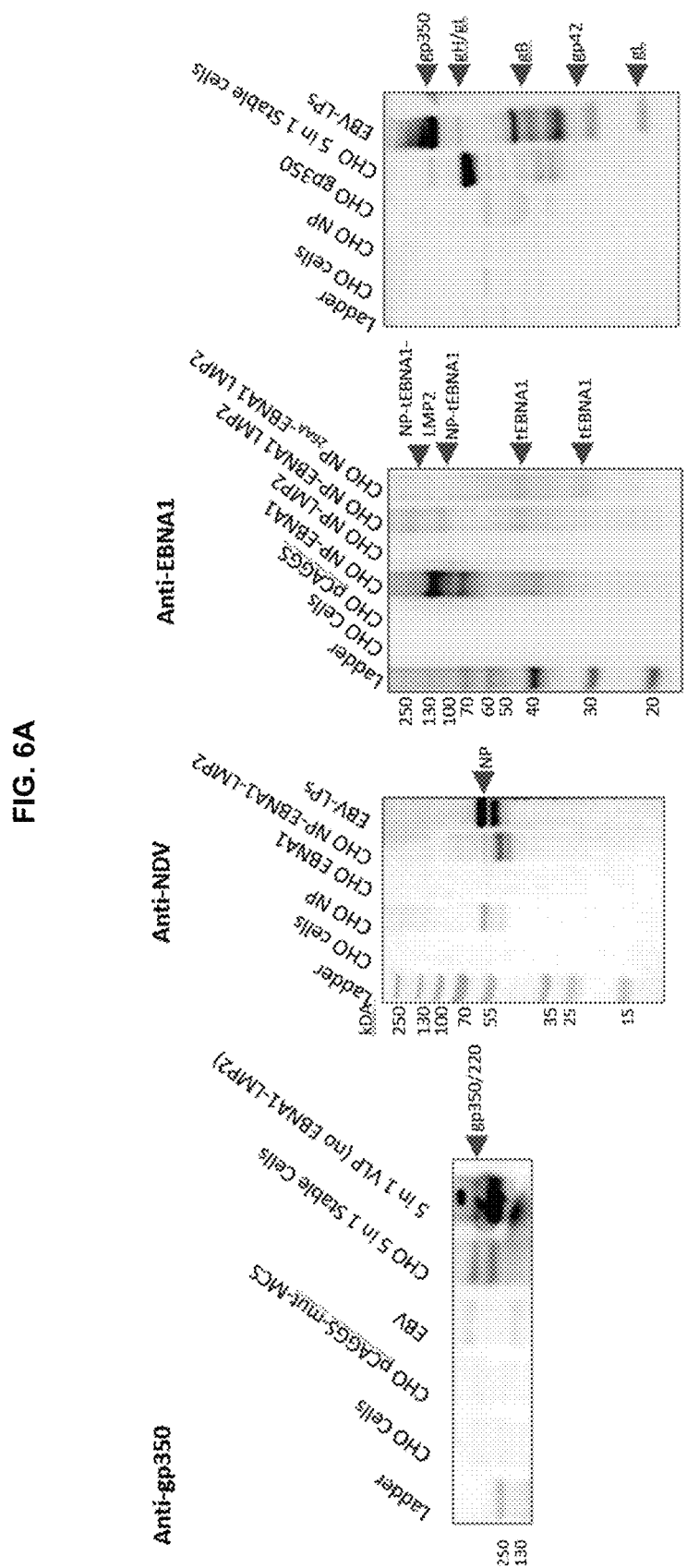
FIGS. 6A-6B show immunoblot analysis of transfected cells and purified EB VLPs.

FIG. 6A shows that partial characterization of the components of EB VLPs (gp350-gB-gp42-gL-gH NDV M, and full-length NP) were analyzed by staining the blot with anti-gp350 (72A1) left panel, or polyclonal anti-NDV middle panel and mAb anti-EBNA1 right panel. A panel to the left (anti-gp350), untransfected CHO cells, CHO cells transfected with pCAGGS plasmids served as negative control. Purified EBV lysate and stable CHO cells expressing EBV five glycoproteins (CHO 5 in 1) served as positive control. Middle panel, presence of NDV NP was analyzed by staining the blot with polyclonal anti-NDV. CHO cells transfected with pCAGGS-NP (CHO-NP), -NP-EBNA1-LMP2 or -26aa-EBNA1-LMP2 served as positive controls. Untransfected CHO cells, CHO cells transfected with pCAGGS-EBNA1 served as negative controls. In the right panel, blots were stained with anti-EBNA1 which detected various isoforms of EBNA1 in CHO cells transfected with pCAGGS-EBNA1, -NP-EBNA1, -NP-EBNA1-LMP2, and NP26AA-EBNA1 LMP2. Untransfected cells and CHO cells transfected with pCAGGS alone served as negative controls.

Figure 6B:
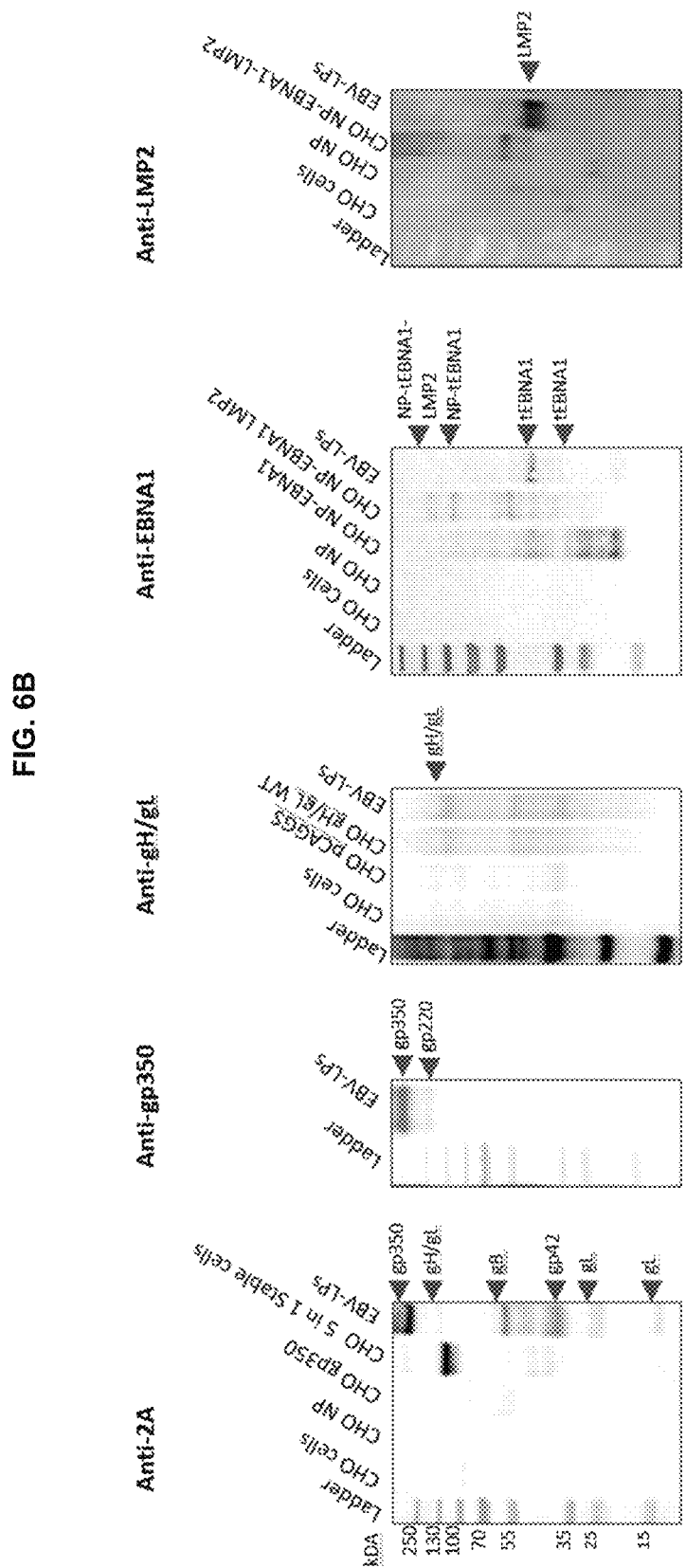
Figure 7:
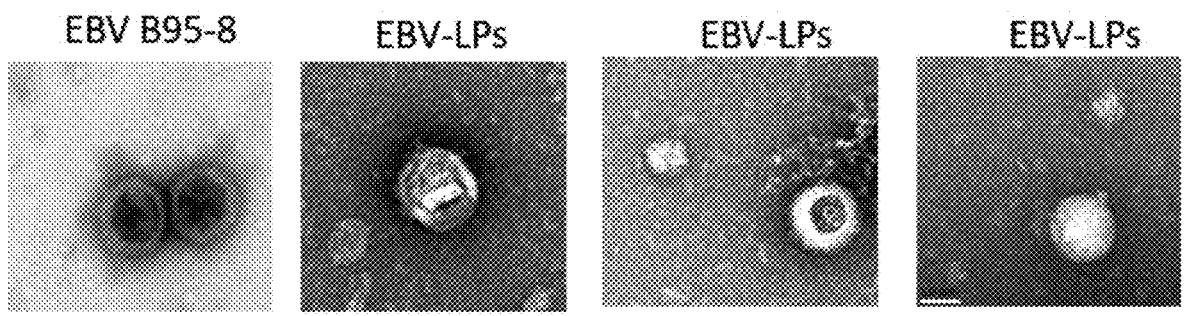
FIG. 7 shows the transmission electron microscopy analysis comparing morphology of purified EB VLPs and wild type EBV (B95-8). Panels show uranyl acetate negatively stained EB VLPs which exhibit particle sizes from 70 nm to 100 nm in diameter, and a structure that resembles the morphology, shape and surface appearance of a purified EBV virions.
Figure 8:
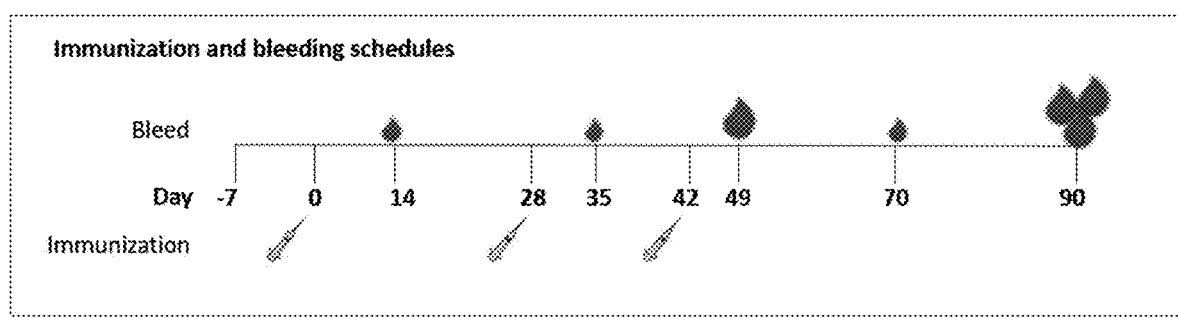
FIG. 8 shows immunization and bleeding schedule of wild type New Zealand white rabbits. 10-12 week-old female and male wild type New Zealand white rabbits (n=6/treatment) from Pocono Rabbit Farm & Laboratory, Inc. (Canadensis, PA) were immunized subcutaneously three times at Days 0, 28, and 42 with 50 μg of purified EB VLPs (gp350-gB-gp42-gL-gH-EBNA1-LMP2) suspended in 0.2 ml TNE buffer adsorbed to 500 μg aluminum hydroxide (alum) and 50 μg monophosphoryl lipid A from Salmonella enterica serotype minnesota Re 595 (MPL). 50 μg of purified UV-inactivated EBV, or 25 μg pf purified EBV gp350 ectodomain (4-863) protein adsorbed to alum and MPL served as positive controls, while 0.2 ml TNE buffer adsorbed to alum and MPL served as a negative control. To assess short-, mid-, and long-term nAb responses, rabbits were bled seven days pre-immunization (pre-bleed), then bled at Day 14, 35, 49, and 70 after primary immunization and humanely euthanized for terminal bleeding at Day 90. Total protein of EB VLPs and UV-inactivated EBV were quantified using Micro BCA™ Protein Assay Kit (ThermoFisher) per the manufacturer's instructions.
Figure 9B:
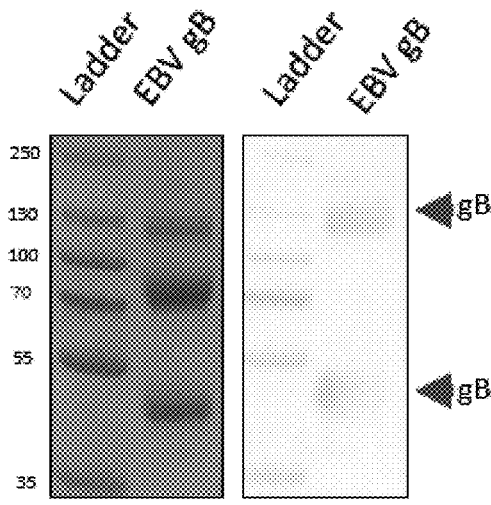
Figure 9B:
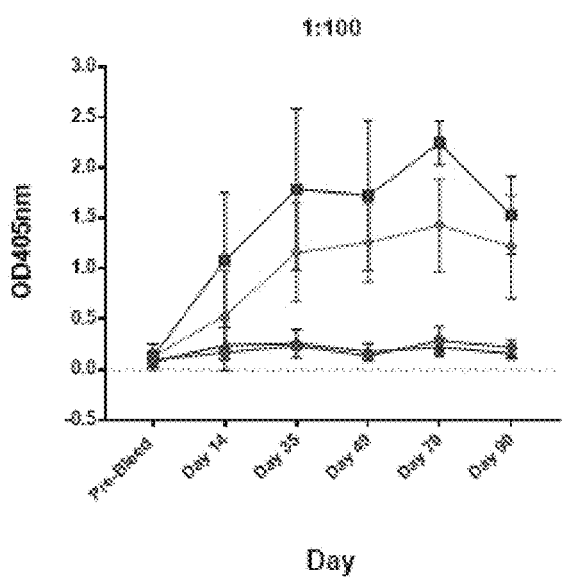
Figure 9B:
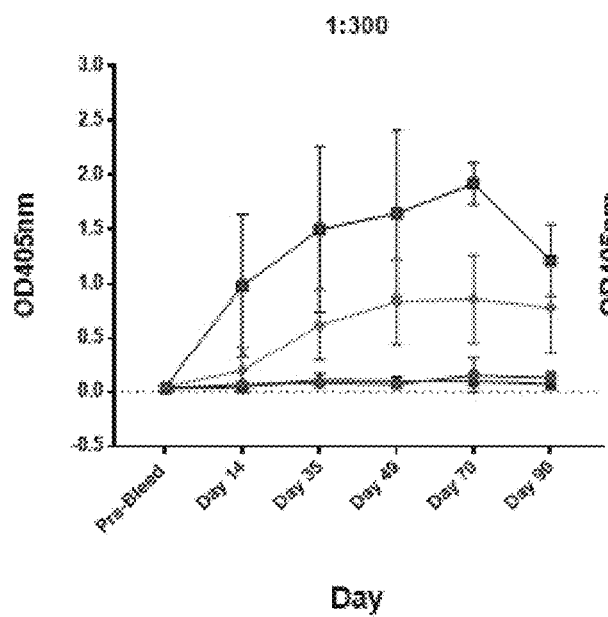
Figure 9B:
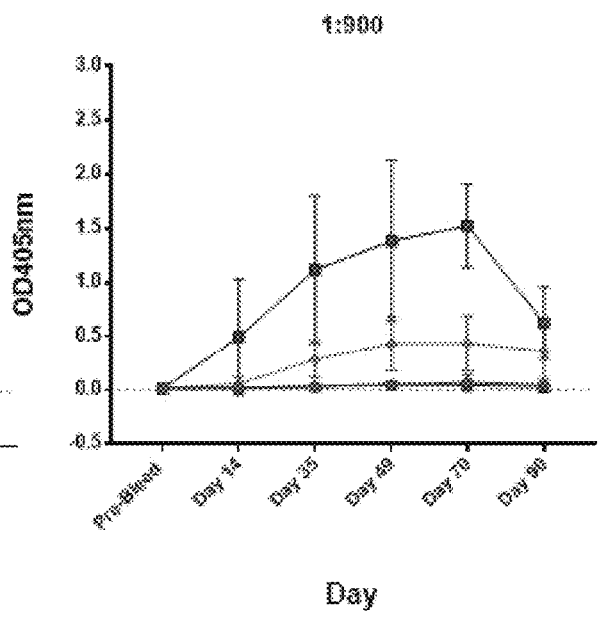
Figure 9C:
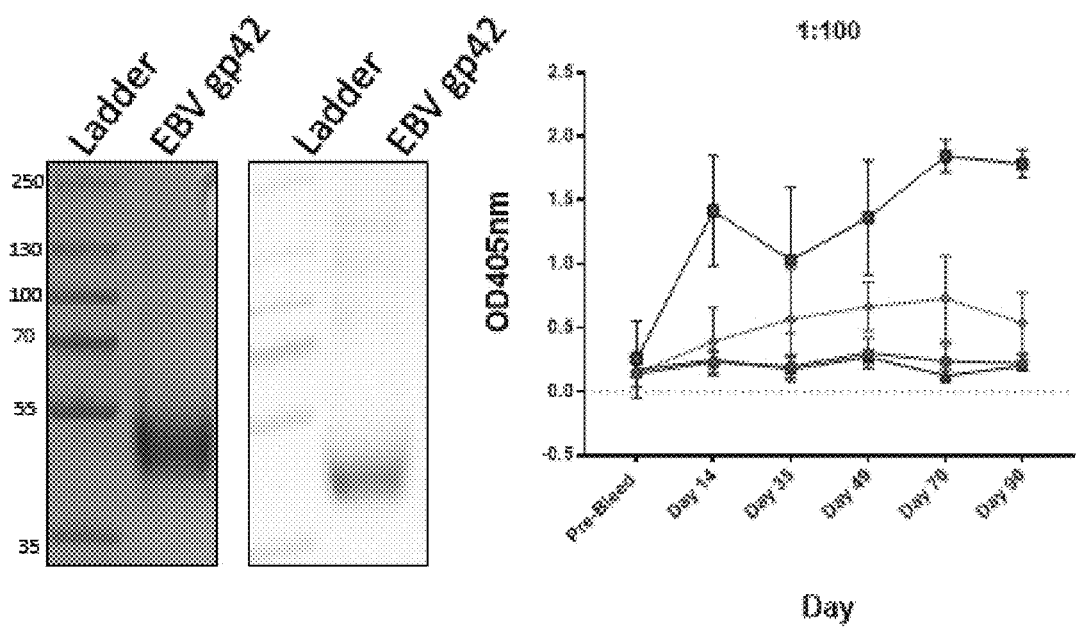
Figure 9C:
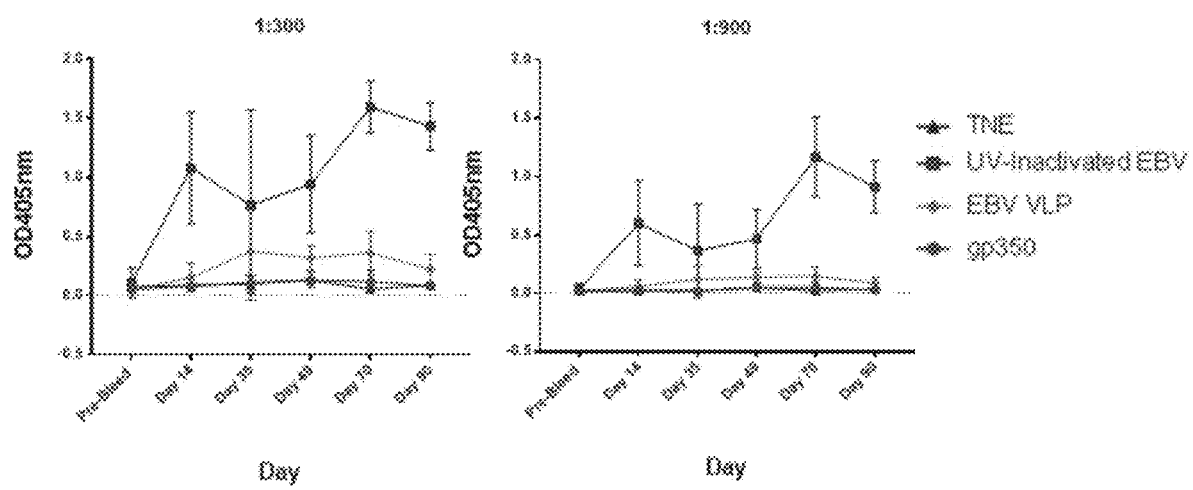
Figure 9D:
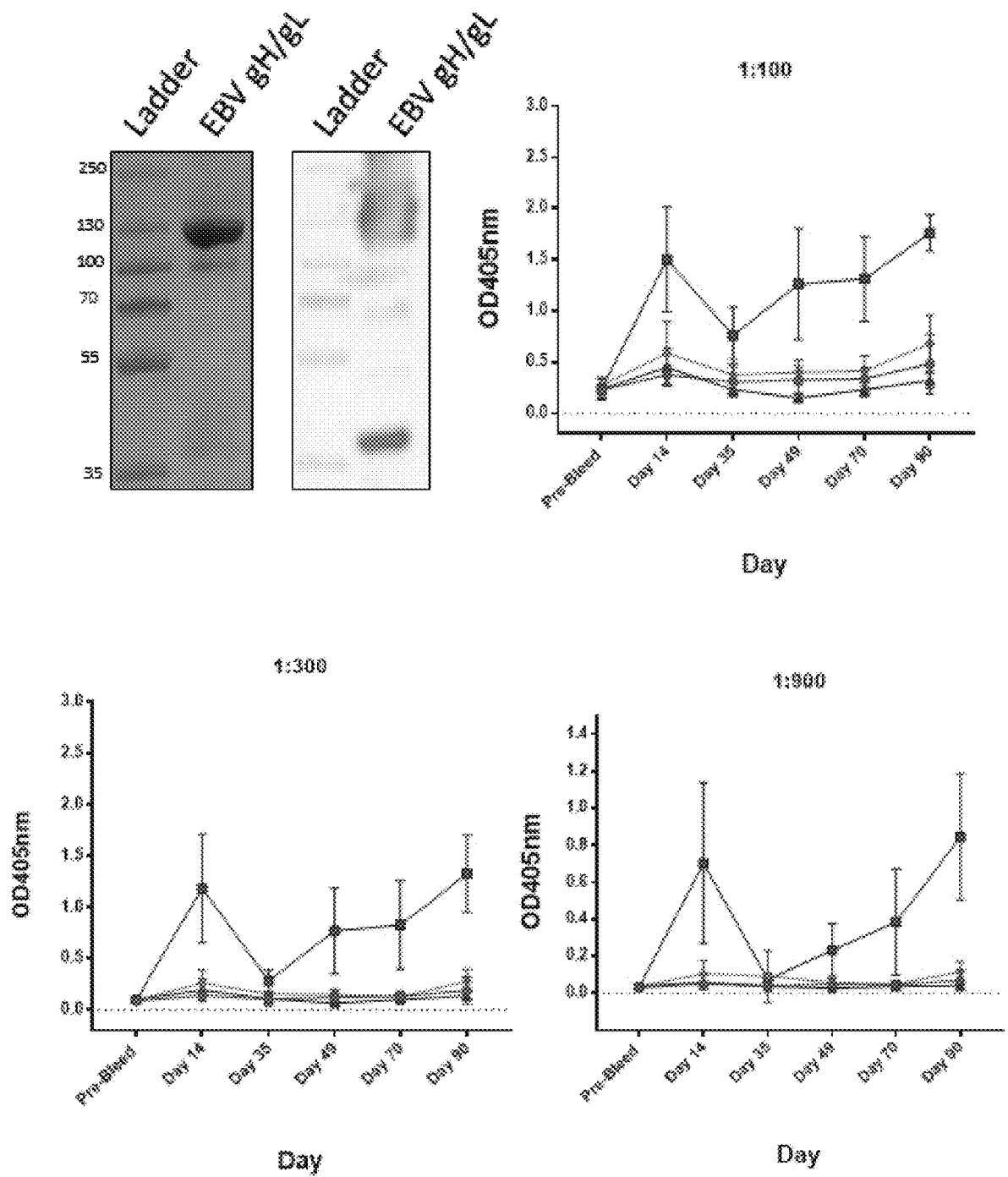
Figure 10:
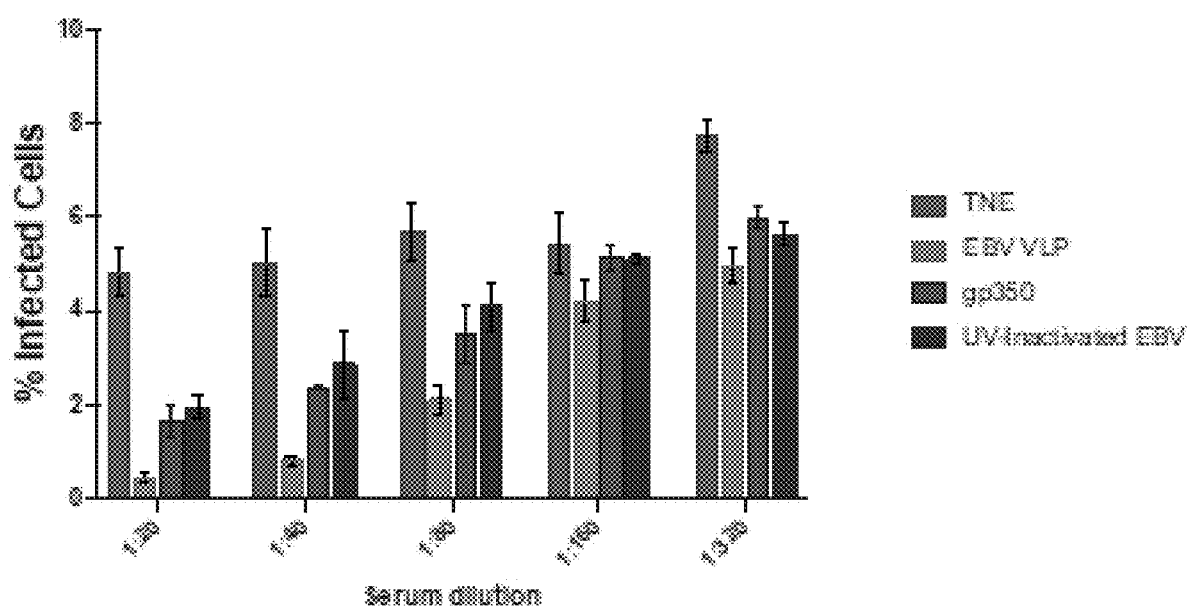
FIG. 10 shows in vitro neutralization assay of EBV to determine immunized rabbits' sera neutralizing antibody responses in HEK-293 cells. For each dilution group, from left to right, the samples are TNE, EB VLP, gp350, and UV-inactivated EBV.

FIG. 6B shows complete characterization of EB VLPs (gp350-gB-gp42-gL-gH-EBNA1-LMP2). Rabbit polyclonal anti-2A, mAb anti-gp350 (72A1), or mAb anti-gH/gL (made in our laboratory) were used to detect all EBV glycoproteins incorporated on VLPs, first three panels to the left. Untransfected CHO cells, CHO cells transfected with pCAGGS alone, pCAGGS gp350, pCAGGS gH/gL or purified EBV served as positive and negative controls. Anti-EBNA1 or anti-LMP2 (14B7) were used to detect EBNA1 and LMP2 incorporated in the EB VLPs in the two panels to the right. Un-transfected CHO cells and CHO cells transfected with pCAGGS-NP, served as negative controls. CHO cells transfected with pCAGGS-NP-EBNA1, or -NP-EBNA-LMP2 served as positive controls. Rabbit polyclonal anti-NDV to detect NP protein was a gift of Dr. T. Morrison, University of Massachusetts Medical School, Worcester, MA), and anti-DNA binding domain EBNA1 mAb was a gift of F. Grässer, Institut für Virologie, Germany). Anti-LMP2 (clone 14B7) was purchased from Santa Cruz.

Example 5: Immune Responses of EB VLPs

As shown in FIG. 8, 10-12 week-old female and male wild type New Zealand white rabbits (n=6/treatment) from Pocono Rabbit Farm & Laboratory, Inc. (*Canadensis*, PA) were immunized subcutaneously three times at Days 0, 28, and 42 with 50 µg of purified EB VLPs (gp350-gB-gp42-gL-gH-EBNA1-LMP2) suspended in 0.2 ml TNE buffer adsorbed to 500 µg aluminum hydroxide (alum) and 50 µg monophosphoryl lipid A from *Salmonella enterica* serotype minnesota Re 595 (MPL). 50 µg of purified UV-inactivated EBV, or 25 µg pf purified EBV gp350 ectodomain (4-863) protein adsorbed to alum and MPL served as positive controls, while 0.2 ml TNE buffer adsorbed to alum and MPL served as a negative control. To assess short-, mid-, and long-term nAb responses, rabbits were bled seven days pre-immunization (pre-bleed), then bled at Day 14, 35, 49, and 70 after primary immunization and humanely euthanized for terminal bleeding at Day 90. Total protein of EB VLPs and UV-inactivated virus were quantified using Micro BCA™ Protein Assay Kit (ThermoFisher) per the manufacturer's instructions.

IgG titers were measured by ELISA using purified soluble gp350, gH/gL, gp42, or gB as target antigens (see commassie blue blots for purity of the proteins). First, 96-well microtiter plates (Nunc-Immuno Plate Maxisorp) were coated with 50 ng/well of the target antigen in PBS buffer (pH 6.2) at 4° C. overnight and blocked with 1% BSA. Sera from immunized rabbits were serially diluted in PBS (1:100, 1:300, 1:900, 1:2700, 1:8100), added to the plate and incubated for 2 hours at room temperature (RT) and the plates were washed three times. Antibody binding was detected with HRP-labeled anti-rabbit IgG secondary antibody after incubation at RT for 1 hour. Plates were washed 3 times and the substrate 2,2'-azino-bis(3-ethylbenzothiazoline-6-sulphonic acid; ABTS Sera Care) was added. The reactions were stopped with ABTS stop solution (Sera Care). To determine antibody titer, optical density (OD) for each protein was read at 405 nm with an ELISA reader (Filermax®) F3, Molecular Devices). ELISA assay was performed for each bleed per animal in quadruplicate and repeated at least three times. Results are expressed as mean±standard deviations (SD). Coomassie stain and immunoblot analysis of EBV glycoprotein gp350, gB, gp42 and gH/gL FC-His tagged recombinant EBV glycoproteins were expressed in HEK-293 cells and purified by protein A column. Results are shown in FIG. 9.

In vitro neutralization assay of EBV was performed to determine immunized rabbits' sera neutralizing antibody responses. Day 49 pooled sera from n=6 from each treatment groups were serially diluted (1:40, 1:80, 1:160 and 1:320) and incubated with purified EBV-eGFP virus, followed by incubation with either epithelial cells (HEK-293) or B cells (Raji) for 1 hour at 37° C. The virus/sera mixture was removed, cells washed three times and incubated for 48 hours and GFP+ cells representing EBV-eGFP infection were enumerated by flow cytometry. Sera from the TNE group was used as the negative control and to normalize EBV-eGFP percent infectivity. Neutralizing activity elicited by the EB VLPs vaccine was comparable to those elicited by the positive control, wild type EBV. The neutralization activity of sera from purified recombinant EBV gp350 ectodomain were significantly lower than those of wild type EBV and EB VLPs.

Figure 11A:
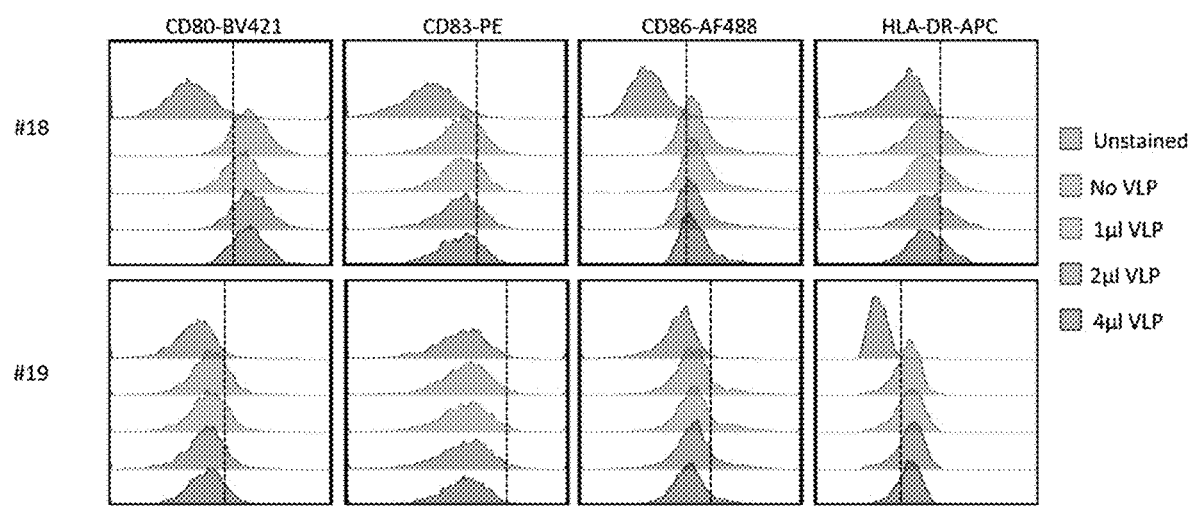
FIGS. 11A-11C show assessment of dendritic cells maturation pulsed with EB VLPs and their ability to stimulate CD4+ and CD8+ T cells.
Figure 11B:
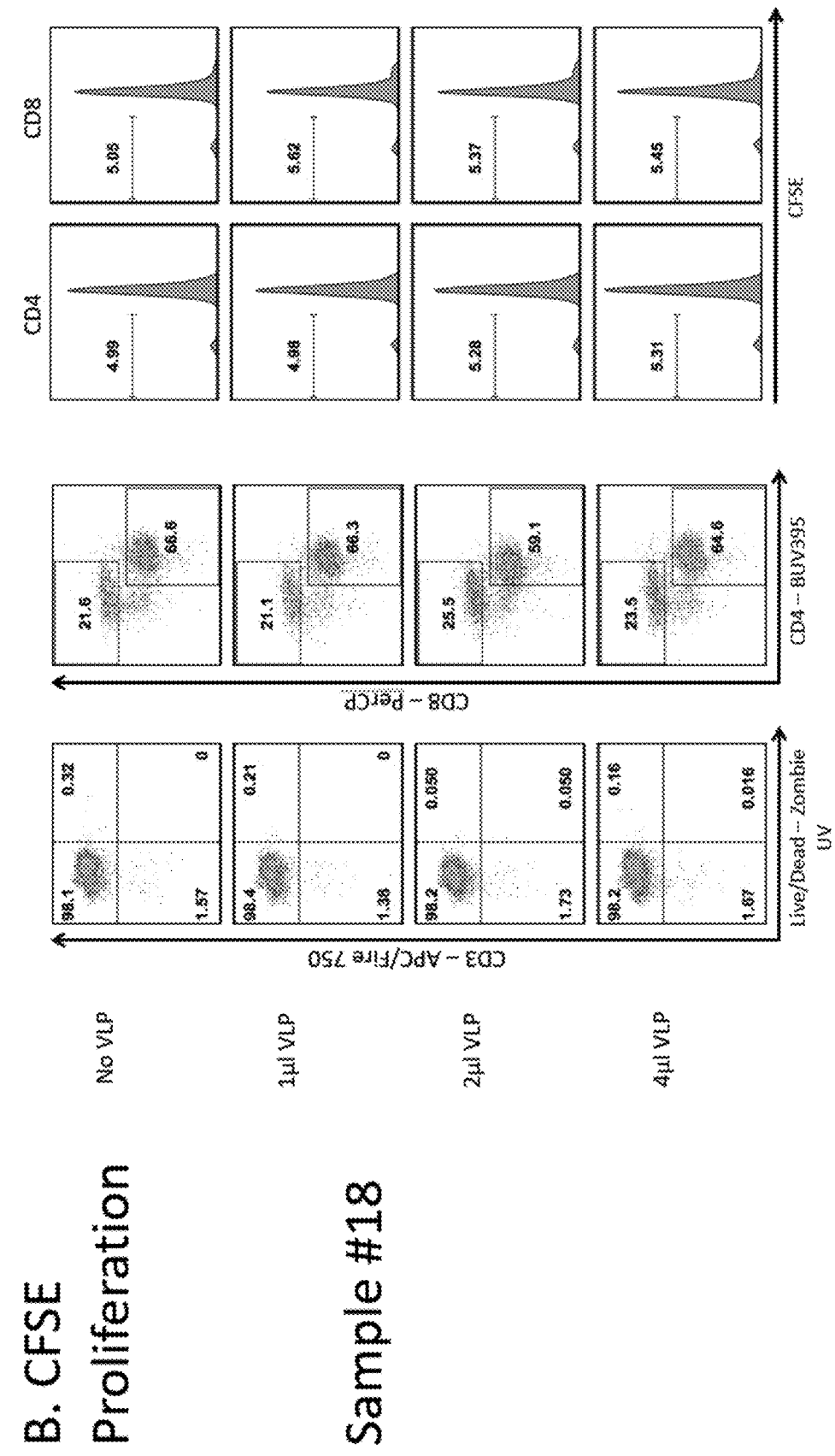
Figure 11C:
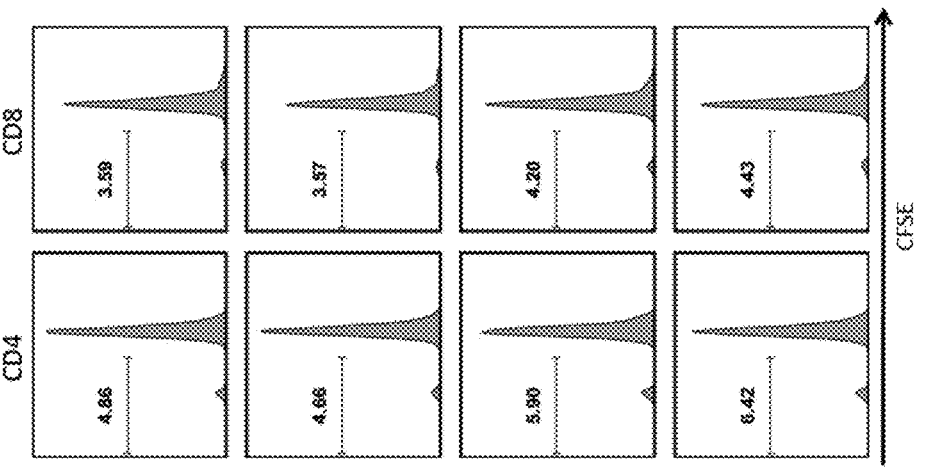
Figure 11C:
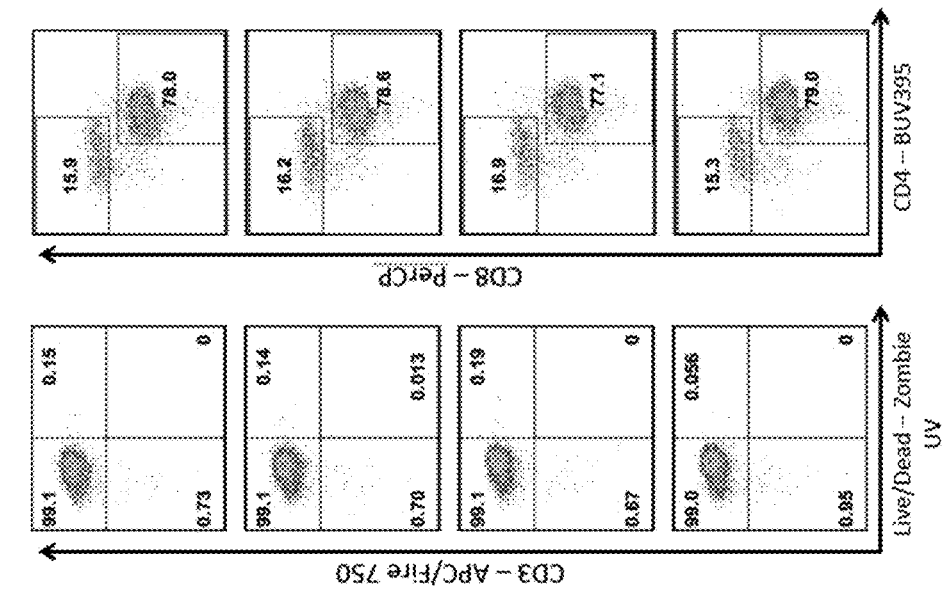

Dendritic cells maturation pulsed with EB VLPs and their ability to stimulate CD4+ and CD8+ T cells were assessed. As shown in FIG. 11A, dendritic cells (DCs) were generated from monocytes isolated from human PBMC samples. Monocytes were maintained in culture with 100 ng/ml GM-CSF and 25 ng/ml IL-4 for 7 days to induce differentiation into DCs. Differentiated DCs were stained with anti-CD14 (FITC), anti-CD83 (PE), and anti-HLA-DR (APC) and analyzed by flow cytometry before being co-cultured with autologous purified T-cells. As shown in FIGS. 11B and 11C, DCs pulsed with EB VLPs were co-cultured with autologous T-cells labeled with CFSE (TC to DC ratio of 60:1). On Day 7 T-cells were re-stimulated with either LPS (100 ng/ml), a pool of 25 EBV-specific peptides (50 ng/ml per peptide), or DCs freshly pulsed with EB VLPs (2.5 µl). Cultures were analyzed after 24 hours for CD4+ (BUV395) and CD8 expression (CFSE), and IFN-γ production (AF-700). Brefeldin A was included in the cultures for the final 5 hours before analysis to block cytokines release. EB VLPs stimulated CD8 T cell proliferation compared to unstimulated cells or cells stimulated with LPS or EBV peptides (data not shown).

Example 6: Immunogenicity of VLPs in Humanized NSG-BLT Mice

Figure 12:
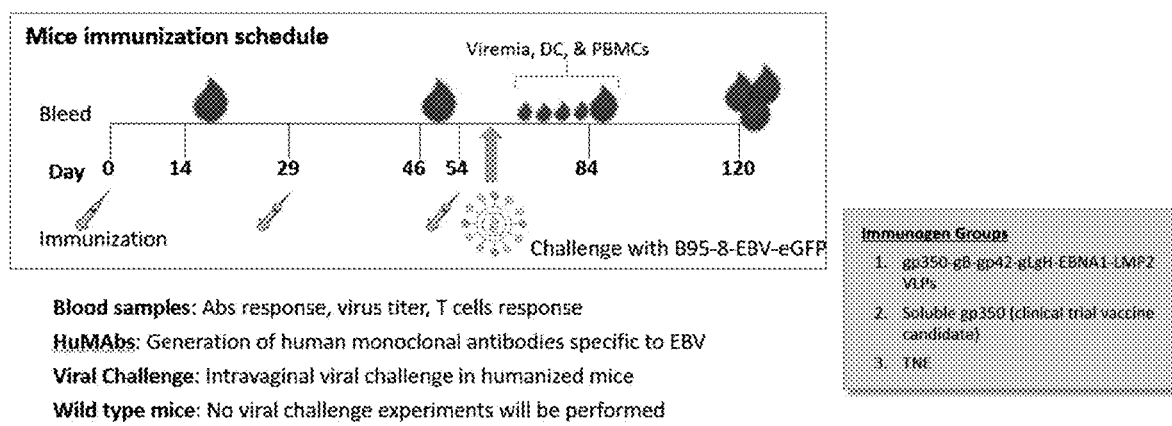
FIG. 12 shows the immunization and bleeding schedules of humanized NSG-BLT mice. 10-12 week-old humanized mice (n=5/treatment) from University of Massachusetts Medical School were immunized intraperitoneally three times at Days 0, 28, and 42 with 50 μg of purified EB VLPs suspended in 0.5 ml TNE buffer adsorbed to 500 μg aluminum hydroxide (alum) and 50 μg monophosphoryl lipid A from *Salmonella enterica* serotype minnesota Re 595 (MPL). Purified 50 μg of UV-inactivated EBV, or 25 μg of purified EBV gp350 ectodomain adsorbed to alum and MPL served as positive control, while 0.5 ml TNE adsorbed to alum and MPL served as negative control. To assess short-, mid-, and long-term nAb responses, mice were bled seven days pre-immunization, then bled at Day 14, 35, and 49 after primary immunization and then humanely euthanized for terminal bleeding at Day 60. Data not shown for the evaluation of EBV-specific IgG antibodies responses generated in EB VLPs immunized huNSG-BLT mice, in vitro neutralization and the animal challenge with EBV to assess in vivo correlates of immune protection. Total protein of EB VLPs and UV-inactivated virus were quantified using Micro BCA™ Protein Assay Kit (ThermoFisher) per the manufacturer's instructions (data not shown).

FIG. 12 shows immunization and bleeding schedules of humanized NSG-BLT mice. The method was describe in the previous publication by Fujiwara et al.[25] 10-12 week-old humanized mice (n=5/treatment) from University of Massachusetts Medical School were immunized intraperitoneally three times at Days 0, 28, and 42 with 50 µg of purified EB VLPs suspended in 0.5 ml TNE buffer adsorbed to 500 µg aluminum hydroxide (alum) and 50 µg monophosphoryl lipid A from *Salmonella enterica* serotype minnesota Re 595 (MPL). Purified 50 µg of UV-inactivated EBV, or 25 µg of purified EBV gp350 ectodomain adsorbed to alum and MPL served as positive control, while 0.5 ml TNE adsorbed to alum and MPL served as negative control. To assess short-, mid-, and long-term nAb responses, mice were bled seven days pre-immunization, then bled at Day 14, 35, and 49 after primary immunization and then humanely euthanized for terminal bleeding at Day 60. Total protein of EB VLPs and UV-inactivated virus were quantified using Micro BCA™ Protein Assay Kit (ThermoFisher) per the manufacturer's instructions. The immune responses in immunized huNSG mice and hu-NSG-BLT mice, including immunoglobulin IgM and IgG antibody responses, CD4+ and CD8+ T cell responses, are monitored to evaluate the therapeutic effects of the VLPs.

Example 7: Co-Expression of EB VLP Subunits

Figure 13A:
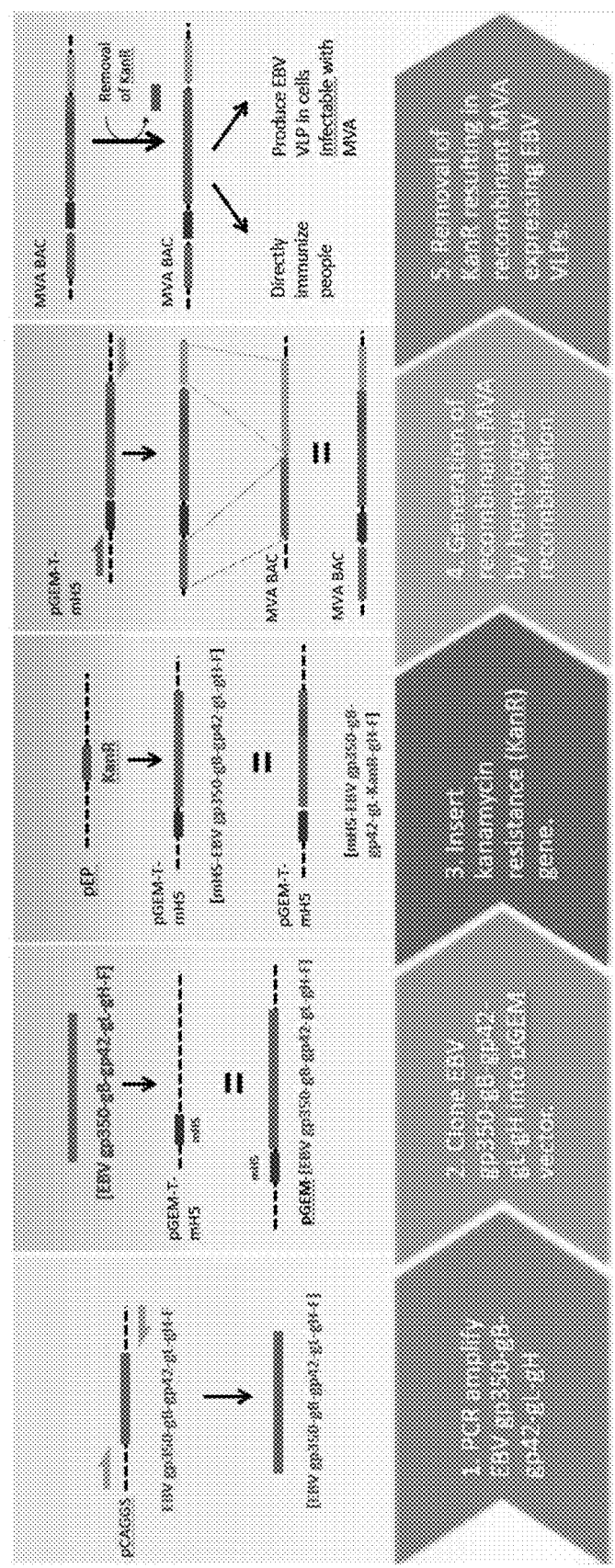
FIGS. 13A-13B illustrate the cloning strategy of EBV gp350-gB-gp42-gL-gH in MVA-BAC.

Modified vaccinia Ankara (MVA) has high safety profile, including immunosuppressed individuals. As shown in FIG. 13A, the first step is PCR amplification of EBV gp350-gB-gp42-gL-gH from PCAGGS using primers with engineered restriction site for cloning into transfer vector. The second step is ligation of EBV gp350-gB-gp42-gL-gH PCR fragment into pGEM transfer vector containing an mH5 promoter, multiple cloning site (MCS) and transcription termination signal (TS). The third step is insertion of Kanamycin resistance marker gene (KanR) and a I-SceI restriction site flanked by 50 bp gB duplicate sequence. The fourth step is PCR amplification of mH-EBV gp350-gB-gp42-gL-gH-TS using primers with 50 bp MVA duplicate sequence overhangs. PCR product is inserted into MVA-BAC via a first Red recombination utilizing the 50 bp MVA overhangs sequence. The fifth step is the Kan selection marker removed from the new MVA construct by introducing a double-strand break at the I-SceI site and followed by a second Red recombination between the 50 bp gB sequence duplication.

Figure 13B:
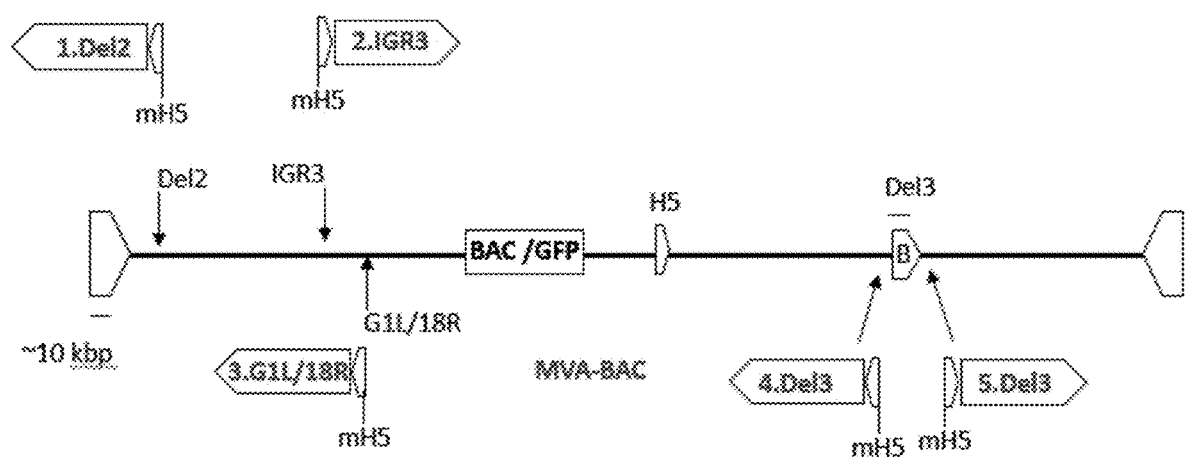

FIG. 13B shows an MVA-BAC construct (not to scale) illustrating the five gene insertion sites (1) Del2, (2) IGR3, (3) G1L/18R) and (4-5) Del3, going in different orientations. Table 1 below summarizes 4 different MVA-EBV constructs, including the gene insertion sites on MVA-BAC vector. EBV genes were inserted in the following order: construct 1: G1L/18R (Wild type EBV-gp350-gB-gp42-gL-gH) and Del 3 (26aa-NP-EBNA1-LMP2); construct 2: G1L/18R (EBV-gp350-gB-gp42-gL-gH VLPs) and Del 3 (M-NP); construct 3: G1L/18R (EBV-gp350-gB-gp42-gL-gH VLPs), Del 3 (26aa-NP-EBNA1-LMP2) and IGR3 (M); and construct 4: G1L/18R (EBV-gp350-gB-gp42-gL-gH VLPs), Del 3 (26aa-NP-EBNA1-LMP2), IGR3 (M) and Del 2 (BMRF2/BDLF2).

TABLE 1

| MVA-BAC EBV Constructs | | | | |
| --- | --- | --- | --- | --- |
| Insertion Site | Construct 1 | Construct 2 | Construct 3 | Construct 4 |
| Del2 | | | | BMRF2/BDLF2 |
| IGR3 | | | M | M |
| G1L/18R | Wild type EBV-gp350-gB-gp42-gL-gH | EBV-gp350-gB-gp42-gL-gH VLPs | EBV-gp350-gB-gp42-gL-gH VLPs | EBV-gp350-gB-gp42-gL-gH VLPs |
| Del3 | 26aa-NP-EBNA1-LMP2 | M-NP | 26aa-NP-EBNA1-LMP2 | 26aa-NP-EBNA1-LMP2 |

Figure 14:
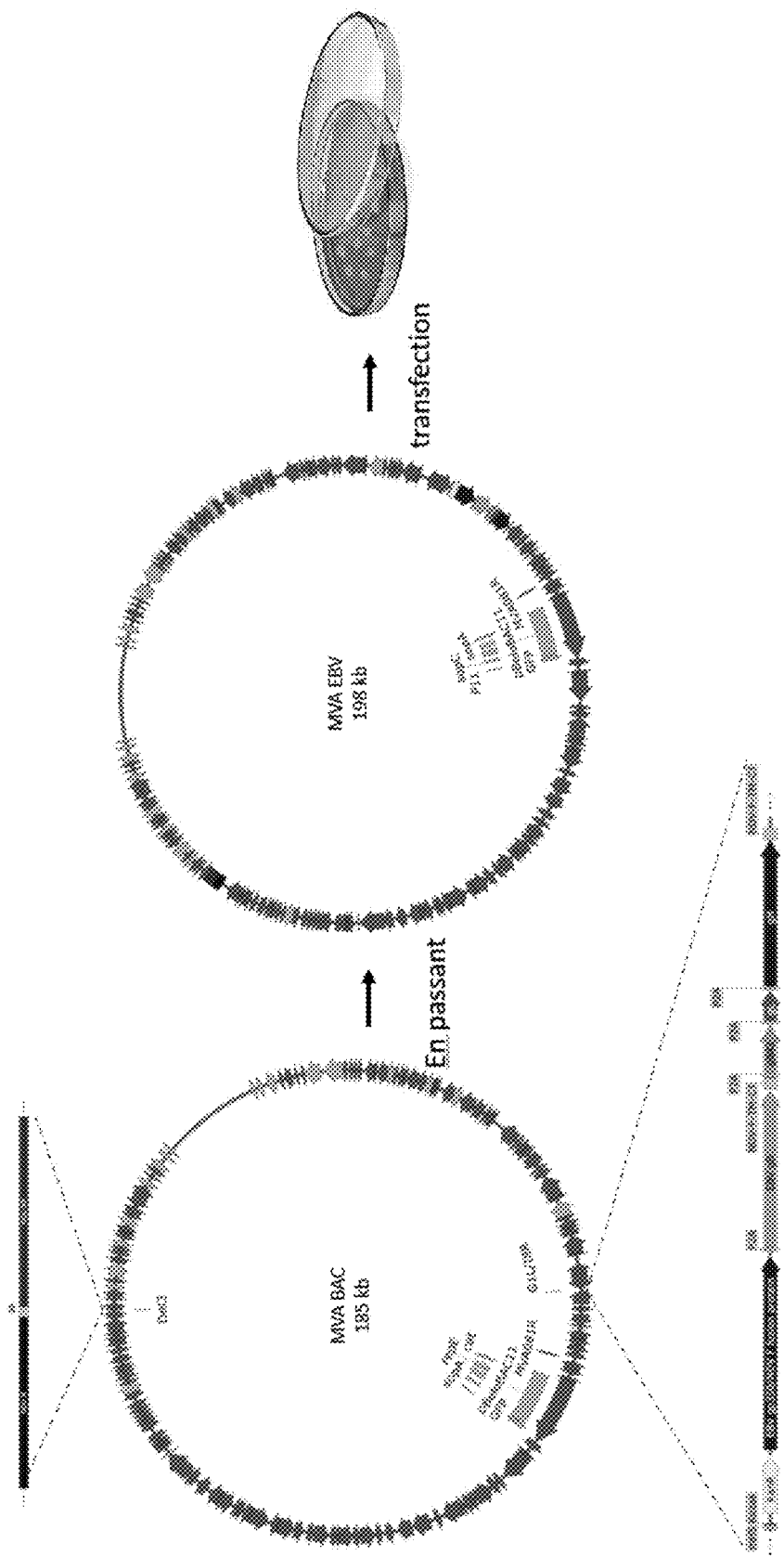
FIG. 14 shows a diagram of cloning and expression of EBV genes in MVA-BAC. Schematic representation of the cloning strategy used to generate MVA-EBV constructs. EBV-gp350-gB-gp42-gL-gH VLPs and M-NP were PCR amplified from respective donor vectors using PCR with 50 bp overhangs homologous to the 5' and 3' end of G1L/18R and Del3 gene insertion sites, respectively. En Passant cloning technique was utilized to ligate the EBV-gp350-gB-gp42-gL-gH VLPs and M-NP PCR products into the MVA-BAC vector containing the pBeloc11 construct and a GFP gene which will be used as an indicator of transfection efficiency. The resulting clone, MVA-EBV was transfected into Baby hamster kidney (BHK)-21 cell or chicken embryo fibroblast (CEF cells). Similar strategy was used to generate wild type MVA expressing EBV-gp350-gB-gp42-gL-gH and modified EBV EBNA1 and LMP2 as candidate vaccine.

FIG. 14 is a schematic representation of the cloning strategy to generate MVA-EBV constructs. Wild type EBV gp350-gB-gp42-gL-gH or EBV-gp350-gB-gp42-gL-gH VLPs and M-NP are PCR amplified from respective donor vectors using PCR with 50 bp overhangs homologous to the 5' and 3' end of G1L/18R and Del3 gene insertion sites, respectively. En Passant cloning technique is utilized to ligate the Wild type EBV gp350-gB-gp42-gL-gH or EBV-gp350-gB-gp42-gL-gH VLPs and M-NP PCR products into the MVA-BAC vector containing the pBeloc11 construct and a GFP gene which will be used as an indicator of transfection efficiency. The resulting clone, MVA-EBV can be transfected into Baby hamster kidney (BHK)-21 cell or chicken fibroblasts cells (CEF) to produce the virus for further infection/immunization. The MVA-expressing wild type EBV gp350-gB-gp42-gL-gH-EBNA1-LMP2 or MVA-EB-VLP vaccine can be subjected to biochemical characterization and the immune responses tested in various animal models to determine correlation of immune protection (e.g. wild type mice, wild type New Zealand white rabbits, huNSG immunized or non-human primate model) or any other appropriate animal model.

REFERENCES

The references, patents and published patent applications listed below, and all references cited in the specification above are hereby incorporated by reference in their entirety, as if fully set forth herein.

1. Rickinson, A. B. & Kieff, E. Epstein-Barr Virus. in *Fields Virology*, Vol. 2 (eds. Knipe, D. & Howley, P.) 2680-2700 (Lippincott Wilkins and Williams, Philadelphia, 2007).
2. Cohen, J. I., Fauci, A. S., Varmus, H. & Nabel, G. J. Epstein-Barr Virus: An Important Vaccine Target for Cancer Prevention. *Science Translational Medicine* 3, 107fs107-107fs107 (2011).
3. Gu, S. Y., et al. First EBV vaccine trial in humans using recombinant vaccinia virus expressing the major membrane antigen. *Dev Biol Stand* 84, 171-177 (1995).
4. Cohen, J. I. Epstein-barr virus vaccines. *Clin Transl Immunology* 4, e32 (2015).
5. Janz, A., et al. Infectious Epstein-Barr virus lacking major glycoprotein BLLF1 (gp350/220) demonstrates the existence of additional viral ligands. *J Virol* 74, 10142-10152 (2000).
6. Moutschen, M., et al. Phase I/II studies to evaluate safety and immunogenicity of a recombinant gp350 Epstein-Barr virus vaccine in healthy adults. *Vaccine* 25, 4697-4705 (2007).
7. Rees, L., et al. A phase I trial of epstein-barr virus gp350 vaccine for children with chronic kidney disease awaiting transplantation. *Transplantation* 88, 1025-1029 (2009).
8. Sokal, E. M., et al. Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. *Journal of Infectious Diseases* 196, 1749-1753 (2007).
9. Connolly, S. A., Jackson, J. O., Jardetzky, T. S. & Longnecker, R. Fusing structure and function: a structural view of the herpesvirus entry machinery: A structural view of herpesvirus entry machinery. *Nat Rev Microbiol* 9, 369-381 (2011).
10. Wang, X. & Hutt-Fletcher, L. M. Epstein-Barr virus lacking glycoprotein gp42 can bind to B cells but is not able to infect. *Journal of virology* 72, 158-163 (1998).
11. Molesworth, S. J., Lake, C. M., Borza, C. M., Turk, S. M. & Hutt-Fletcher, L. M. Epstein-Barr virus gH is essential for penetration of B cells but also plays a role in attachment of virus to epithelial cells. *Journal of virology* 74, 6324-6332 (2000).
12. Kim, J. H., et al. High cleavage efficiency of a 2A peptide derived from porcine teschovirus-1 in human cell lines, zebrafish and mice. *PLoS One* 6, e18556 (2011).
13. Babcock, G. J., Decker, L. L., Volk, M. & Thorley-Lawson, D. A. EBV persistence in memory B cells in vivo. *Immunity* 9, 395-404 (1998).
14 Goedert, J. J., et al. Spectrum of AIDS-associated malignant disorders. *Lancet* 351, 1833-1839 (1998).
15. Miller, N. & Hutt-Fletcher, L. M. A monoclonal antibody to glycoprotein gp85 inhibits fusion but not attachment of Epstein-Barr virus. *J Virol* 62, 2366-2372 (1988).
16. Cui, X., et al. Rabbits immunized with Epstein-Barr virus gH/gL or gB recombinant proteins elicit higher serum virus neutralizing activity than gp350. *Vaccine* (2016).
17. Perez, E. M., Foley, J., Tison, T., Silva, R. & Ogembo, J. G. Novel Epstein-Barr virus-like particles incorporating gH/gL-EBNA1 or gB-LMP2 induce high neutralizing antibody titers and EBV-specific T-cell responses in immunized mice. *Oncotarget* 8, 19255-19273 (2017).
18. Ruiss, R., et al. A virus-like particle-based Epstein-Barr virus vaccine. *J Virol* 85, 13105-13113 (2011).
19. Pavlova, S., et al. An Epstein-Barr virus mutant produces immunogenic defective particles devoid of viral DNA. *J Virol* 87, 2011-2022 (2013).
20. Germain, R. N. Immunology. The ins and outs of antigen processing and presentation. *Nature* 322, 687-689 (1986).
21. Ray, G., Schmitt, P. T. & Schmitt, A. P. C-Terminal DxD-Containing Sequences within Paramyxovirus Nucleocapsid Proteins Determine Matrix Protein Compatibility and Can Direct Foreign Proteins into Budding Particles. *J Virol* 90, 3650-3660 (2016).
22. Ogembo, J. G., et al. A chimeric EBV gp350/220-based VLP replicates the virion B-cell attachment mechanism and elicits long-lasting neutralizing antibodies in mice. *J Transl Med* 13, 50 (2015).
23. Jangalwe, S., Shultz, L. D., Mathew, A. & Brehm, M. A. Improved B cell development in humanized NOD-scid IL2Rgammanull mice transgenically expressing human stem cell factor, granulocyte-macrophage colony-stimulating factor and interleukin-3. *Immun Inflamm Dis* 4, 427-440 (2016).
24. Ogembo, J. G., et al. Human complement receptor type 1/CD35 is an Epstein-Barr Virus receptor. *Cell Rep* 3, 371-385 (2013).
25. Fujiwara S., et al., Modeling EBV infection and pathogenesis in new-generation humanized mice. *Exp. Mol. Med.* 47: e135 (2015).

SEQUENCE LISTING

Sequence total quantity: 5
SEQ ID NO: 1          moltype = AA  length = 7
FEATURE               Location/Qualifiers
source                1..7
                      mol_type = protein
                      organism = synthetic construct

```
SEQUENCE: 1
GAAGAGA                                                                  7

SEQ ID NO: 2           moltype = AA  length = 489
FEATURE                Location/Qualifiers
source                 1..489
                       mol_type = protein
                       organism = synthetic construct
SEQUENCE: 2
MSSVFDEYEQ LLAAQTRPNG AHGGGEKGST LKVEVPVFTL NSDDPEDRWN FVVFCLRIAV     60
SEDANKPLRQ GALISLLCSH SQVMRNHVAL AGKQNEATLA VLEIDGFTNS VPQFNNTSGV    120
SEERAQRFMM IAGSLPRACS NGTPFITAGV EDDAPEDIID TLERILSIQA QVWVTVAKAM    180
TAYETADESE TRRINKYMQQ GRVQKKYILH PVCRSAIQLT IRQSLAVRIF LVSELKRGRN    240
HAGGSSTYYN LVGDVDSYIR NTGLTAFFLT LKYGINTKTS ALALSSLAGD IQKMKQLMRL    300
YRMKGDNAPY MTLLGDSDQM SFAPAEYAQL YSFAMAMASV LDKGTGKYQF ARDFMSTSFW    360
RLGVEYAQAQ GSSINEDMAA ELKLTPAARR GLAAAAQRVS EETSSMDIPT QQAGVLTGLS    420
DGGPQAPQGG SNRSQGRPDA GDGETQFLDL MRAVANSMRE APNSVQSTTQ PEPPPTPGPS    480
QDNDTDWGY                                                            489

SEQ ID NO: 3           moltype = AA  length = 26
FEATURE                Location/Qualifiers
source                 1..26
                       mol_type = protein
                       organism = synthetic construct
SEQUENCE: 3
SVQSTTQPEP PPTPGPSQDN DTDWGY                                             26

SEQ ID NO: 4           moltype = AA  length = 4
FEATURE                Location/Qualifiers
source                 1..4
                       mol_type = protein
                       organism = synthetic construct
SEQUENCE: 4
KKKR                                                                     4

SEQ ID NO: 5           moltype = AA  length = 4
FEATURE                Location/Qualifiers
source                 1..4
                       mol_type = protein
                       organism = synthetic construct
SEQUENCE: 5
RKKR                                                                     4
```

The invention claimed is:

1. An expression system for co-expressing a plurality of EBV envelope glycoproteins comprising an expression vector having two or more expression cassettes, wherein each of the two or more expression cassettes comprises:
   a promoter,
   a nucleic acid sequence encoding two or more EBV envelope glycoproteins, and
   one or more linking sequences;
   wherein the two or more EBV envelope glycoproteins are co-expressed simultaneously, self-cleaved and/or self-processed to assemble into one or more glycoprotein complexes.

2. The expression system of claim 1, wherein the plurality of EBV envelope glycoproteins comprises gp350, gB, gp42, gH, and gL.

3. The expression system of claim 1, wherein one or more glycoprotein complexes comprises gp42-gH/gL or gB-gH/gL.

4. The expression system of claim 1, wherein the expression vector is a plasmid vector or a viral vector.

5. The expression system of claim 4, wherein the expression vector is an MVA vector.

6. The expression system of claim 5, wherein the two or more expression cassettes are inserted into two or more insertion sites selected from a Del2 insertion site, an IGR3 insertion site, a G1L/18R insertion site, and a Del3 insertion site.

7. The expression system of claim 1, wherein the one or more linking sequences include one or more 2A sequences encoding 2A peptides that mediate ribosomal skipping.

8. A composition comprising an expression vector having two or more expression cassettes, wherein each of the two or more expression cassettes comprises:
   a promoter,
   a nucleic acid sequence encoding two or more EBV envelope glycoproteins, and
   one or more linking sequences;
   wherein the two or more EBV envelope glycoproteins can are co-expressed simultaneously, self-cleaved and/or self-processed to assemble into one or more glycoprotein complexes; and
   wherein the expression vector is capable of co-expressing a plurality of EBV envelope glycoproteins.

9. The composition of claim 8, wherein the plurality of EBV envelope glycoproteins comprises gp350, gB, gp42, gH, and gL.

10. The composition of claim 8, wherein one or more glycoprotein complexes comprises gp42-gH/gL or gB-gH/gL.

11. The composition of claim 8, wherein the expression vector is a plasmid vector or a viral vector.

12. The composition of claim 11, wherein the expression vector is an MVA vector.

13. The composition of claim 12, wherein the two or more expression cassettes are inserted into two or more insertion sites selected from a Del2 insertion site, an IGR3 insertion site, a G1L/18R insertion site, and a Del3 insertion site.

14. The composition of claim 8, wherein the one or more linking sequences include one or more 2A sequences encoding 2A peptides that mediate ribosomal skipping.

15. The composition of claim 8, further comprising one or more adjuvants.

16. The composition of claim 8, further comprising one or more pharmaceutically acceptable carriers.

17. A method of preventing or treating an EBV infection or a condition associated with an EBV infection comprising administering to a subject in need thereof a therapeutically effective amount of the composition of claim 8.

18. The method of claim 17, wherein the plurality of EBV envelope glycoproteins comprises gp350, gB, gp42, gH, and gL.

19. The method of claim 17, wherein the expression vector is an MVA vector.

20. The method of claim 17, wherein the one or more linking sequences include one or more 2A sequences encoding 2A peptides that mediate ribosomal skipping.

\* \* \* \* \*